(12) United States Patent
Woodard et al.

(10) Patent No.: US 12,383,286 B2
(45) Date of Patent: Aug. 12, 2025

(54) MINIMALLY INVASIVE SURGICAL TOOLS AND SYSTEMS

(71) Applicant: Wright Medical Technology, Inc., Memphis, TN (US)

(72) Inventors: Joseph Ryan Woodard, Memphis, TN (US); Erin Muller, Fort Wayne, IN (US); Terrance W. Strohkirch, Memphis, TN (US); Gary W. Lowery, Eads, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 732 days.

(21) Appl. No.: 17/650,393

(22) Filed: Feb. 9, 2022

(65) Prior Publication Data
US 2022/0313287 A1 Oct. 6, 2022

Related U.S. Application Data

(60) Provisional application No. 63/155,497, filed on Mar. 2, 2021.

(51) Int. Cl.
| | | |
|---|---|---|
| A61B 17/17 | (2006.01) | |
| A61B 17/00 | (2006.01) | |
| A61B 17/56 | (2006.01) | |

(52) U.S. Cl.
CPC .............. *A61B 17/1775* (2016.11); *A61B 2017/00858* (2013.01); *A61B 2017/565* (2013.01)

(58) Field of Classification Search
CPC .......... A61B 17/1775; A61B 17/1782
See application file for complete search history.

(56) References Cited

U.S. PATENT DOCUMENTS

| | | | | |
|---|---|---|---|---|
| 4,911,153 A | * | 3/1990 | Border | A61B 17/1725 606/98 |
| 5,163,940 A | * | 11/1992 | Bourque | A61B 17/1764 606/88 |
| 5,688,284 A | * | 11/1997 | Chervitz | A61B 17/1714 606/88 |
| 6,210,415 B1 | * | 4/2001 | Bester | A61B 17/1714 606/96 |

(Continued)

FOREIGN PATENT DOCUMENTS

| | | |
|---|---|---|
| EP | 3583905 A1 | 12/2019 |
| WO | 2011037885 A1 | 3/2011 |

(Continued)

OTHER PUBLICATIONS

Extended European Search Report issued in connection with Application No. 22159202.5, Jul. 26, 2022, 8 pages.

*Primary Examiner* — Nicholas W Woodall
(74) *Attorney, Agent, or Firm* — DUANE MORRIS LLP

(57) ABSTRACT

A surgical tool includes a body defining an opening sized and configured to receive a first bone portion therein, a displacement tip coupled to a first end of the body, the displacement tip sized and configured for insertion into a medullary canal of a second bone portion, and a deployable retention block configured to be transitioned from a first position to a second position. The deployable retention block is configured to maintain the first bone portion in a predetermined position when the deployable retention block is in the second position.

8 Claims, 25 Drawing Sheets

(56) References Cited

U.S. PATENT DOCUMENTS

| | | |
|---|---|---|
| 6,695,847 B2 | 2/2004 | Bianchetti |
| 2009/0204148 A1 | 8/2009 | Lenke et al. |
| 2009/0234356 A1* | 9/2009 | Bickley ................. A61B 17/68 606/59 |
| 2011/0077656 A1* | 3/2011 | Sand ...................... A61B 17/82 606/86 R |
| 2012/0130383 A1 | 5/2012 | Budoff |
| 2012/0209268 A1* | 8/2012 | Overes ............... A61B 17/1725 606/62 |
| 2014/0194999 A1 | 7/2014 | Orbay et al. |
| 2015/0071885 A1 | 3/2015 | Yong et al. |
| 2017/0196602 A1 | 7/2017 | Lundquist et al. |
| 2019/0142488 A1 | 5/2019 | Wang et al. |
| 2020/0253641 A1 | 8/2020 | Treace et al. |
| 2020/0352581 A1 | 11/2020 | Russi et al. |

FOREIGN PATENT DOCUMENTS

| | | |
|---|---|---|
| WO | 2012162607 A1 | 11/2012 |
| WO | 2017011656 A1 | 1/2017 |
| WO | 2020180598 A1 | 9/2020 |

* cited by examiner

MINIMALLY INVASIVE SURGICAL TOOLS AND SYSTEMS

CROSS-REFERENCE TO RELATED APPLICATION

This application claims priority to U.S. Provisional Patent Application No. 63/155,497, filed Mar. 2, 2021, the entirety of which is incorporated by reference herein.

BACKGROUND

During surgery, such as bunion surgery, it may be necessary to fix a position of a first bone fragment and a second bone fragment. In some instances, an osteotomy is formed in a bone, such as the first metatarsal, to correct one or more defects. After forming the osteotomy, a first fragment of the bone and a second fragment of a bone are positioned to correct the defect and are fixed in place using one or more fixation elements. One or more bone fragments may also be formed as a result of an injury and/or medical procedure.

Current surgical techniques rely on the placement of guide elements, such as k-wires, prior to insertion of the fixation elements. Placement of guide elements is performed by a surgeon and often requires the surgeon to insert and remove the guide element several times before a desired placement is achieved. The repeated insertion and removal of guide elements results in additional wounds in a patient and increases pain, recovery time, and complexity of surgery (including difficulty, increased surgical time, etc.)

SUMMARY

In various embodiments, a surgical tool is disclosed. The surgical tool includes a body defining an opening sized and configured to receive a first bone portion therein, a displacement tip coupled to a first end of the body, the displacement tip sized and configured for insertion into a medullary canal of a second bone portion, and a deployable retention block configured to be transitioned from a first position to a second position. The deployable retention block is configured to maintain the first bone portion in a predetermined position when the deployable retention block is in the second position.

In various embodiments, a targeting guide is disclosed. The targeting guide includes a body extending from a first end to a second end substantially on a first longitudinal axis. The body defines a first guide hole extending from a first surface to a second surface. The targeting guide further includes a guide arm extending from a first end to a second end substantially on a second longitudinal axis. A first end of the guide arm is rotatably coupled to a first end of the body. A targeting arm is coupled to the second end of the guide arm. The targeting arm comprises a body defining a second guide hole. A guide element inserted through the second guide hole is configured to visualize an insertion trajectory of a guide element inserted through the first guide hole.

In various embodiments, a surgical tool is disclosed. The surgical tool includes a handle body extending substantially on a first longitudinal axis, a displacement tip coupled to a first end of the handle body, the displacement tip extending substantially parallel to the first longitudinal axis, an arm extension extending substantially on a second longitudinal axis and having a first end coupled to the handle body, and a targeting arm coupled to a second end of the arm extension and defining at least one guide hole extending therethrough.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

Figure 1:
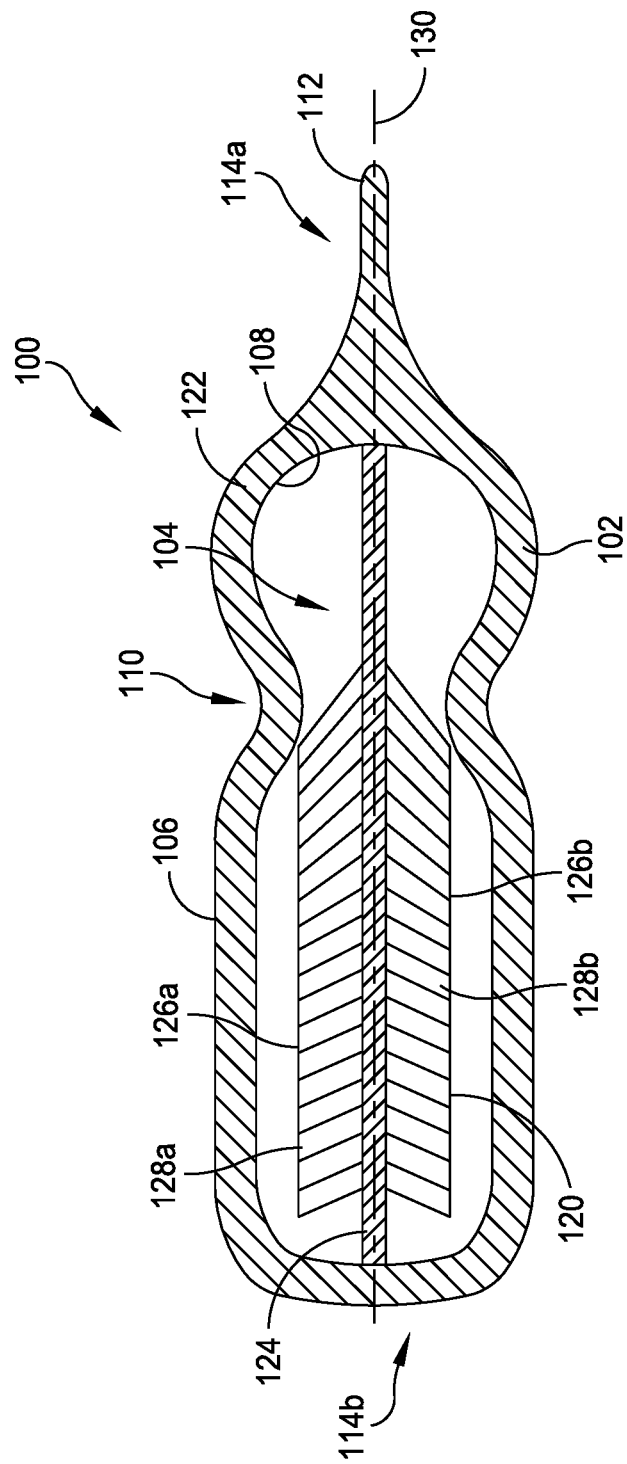
FIG. 1 illustrates a minimally invasive surgery (MIS) displacement translator having an integrated block for retaining a portion of a patient, in accordance with some embodiments.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top," "bottom," "proximal," "distal," "superior," "inferior," "medial," and "lateral" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected," refer to a relationship wherein structures are secured or attached to one another either directly or indirectly through intervening structures, as well as both movable or rigid attachments or relationships, unless expressly described otherwise. Like elements have been given like numerical designations to facilitate an understanding of the present subject matter.

As used herein, the term "substantially" denotes elements having a recited relationship (e.g., parallel, perpendicular, aligned, etc.) within acceptable manufacturing tolerances. For example, as used herein, the term "substantially parallel" is used to denote elements that are parallel or that vary from a parallel arrangement within an acceptable margin of error, such as +/−5°, although it will be recognized that greater and/or lesser deviations can exist based on manufacturing processes and/or other manufacturing requirements.

In various embodiments, minimally invasive surgery (MIS) tools and methods are disclosed. The MIS tools may include one or more of a displacement translator (also referred to herein as an elevator) configured to translate a first bone fragment relative to a second bone fragment. The MIS displacement translators may include a body. The body may define a cavity sized and configured to receive a portion of a patient bone therein. A displacement tip extends from a portion of the body. The displacement tip is sized and configured to be received within the medullary canal of a first bone portion and to allow rotation and/or pivoting of the displacement translator to displace a second bone portion relative to the first bone portion. In some embodiments, the displacement translator includes a bone retention block configured to retain and/or interact with the second bone portion. The bone retention block may be transitioned from a collapsed position to a deployed position.

In some embodiments, the MIS tools include a targeting guide. The targeting guide is configured to facilitate alignment, positioning, and/or insertion of one or more surgical guide elements, such as k-wires. The targeting guide may include a body having one or more positioning elements. The targeting guide is positioned adjacent to a foot and includes one or more guide holes sized and configured to receive a k-wire and/or a k-wire sleeve therethrough. The k-wires are positioned in a predetermined position with respect to the first and second bone portions by the targeting guide.

In some embodiments, the MIS tools include a combination displacement translator and targeting guide. For example, a single tool may include elements of a displacement translator, such as a displacement body, displacement tip, etc. and elements of a targeting guide, such as a targeting arm, guide holes, etc. The combination displacement translator and targeting guide may include a modular construction including multiple connectable components and/or may include a monolithic construction.

FIGS. 1-4 illustrate an MIS displacement translator 100 having an integrated block 120 for retaining a portion of a patient, in accordance with some embodiments. The displacement translator 100 includes a body 102 defining an opening 104 (or inner cavity). In the illustrated embodiment, the body 102 and the opening 104 each have a generally rounded rectangular shape, although it will be appreciated that the body 102 and/or the opening 104 may have any suitable shape, such as, for example, a regular geometric shape (e.g., rectangular, ovoid, etc.) or an irregular shape. The cavity 104 is sized and configured to receive one or more anatomical features of a patient therein. For example, in some embodiments, the cavity 104 is sized and configured to receive a first portion of a patient's toe (including a first portion of a bone). The body 102 extends generally along a longitudinal axis 130 from a first end 114a to a second end 114b.

In some embodiments, the body 102 includes an outer perimeter edge 106 defining an outer perimeter of the body 102 and an inner perimeter edge 108 defining the cavity 104. The outer perimeter edge 106 and the inner perimeter edge 108 may define similar, identical, and/or different shapes. For example, in the illustrated embodiment, the outer perimeter edge 106 and the inner perimeter edge 108 generally define similar profiles such that the inner perimeter edge 108 is curved, straight, etc. adjacent to and/or parallel with portions of the outer perimeter edge 106 that are curved, straight, etc. In the illustrated embodiment, the generally rectangular body 102 defines a compressed or inset portion 110 defined by the both the outer perimeter edge 106 and the inner perimeter edge 108. The compressed portion 110 extends partially into the cavity 104. The compressed portion 110 may be configured to allow flexing of the body 102 at the compressed portion 110.

The body 102 includes a displacement tip 112 positioned at the first end 114a of the body 102 (e.g., a distal end). The displacement tip 112 has a predetermined radius of curvature 115 (see FIG. 2). The displacement tip 112 is sized and configured for insertion into a medullary canal of a bone portion, such as, for example, a medullary canal of a metatarsal having an osteotomy formed therein. The radius of curvature 115 of the displacement tip 112 is configured to allow pivoting of the body 102 with respect to the first bone portion to cause displacement of one or more bone portions (e.g., the first bone portion, a second portion, etc.).

In some embodiments, the displacement translator 100 includes an integrated block 120 sized and configured to retain an anatomical feature of a patient. The integrated block 120 is configured to maintain the anatomical feature in a predetermined position and/or alignment. For example, in some embodiments, the integrated block 120 is configured to maintain a rotated anatomical feature, such as a distal portion of a toe, in a rotated position. The integrated block 120 is configured to interface with a surface of the anatomical feature. In some embodiments, the integrated block 120 includes a surface configured to increase friction between the anatomical feature and the integrated block 120. For example, the surface of the integrated block 120 may include a texture, retention elements (such as divots), a coating, and/or any other suitable element configured to increase friction and prevent movement of the anatomical feature.

Figure 2:
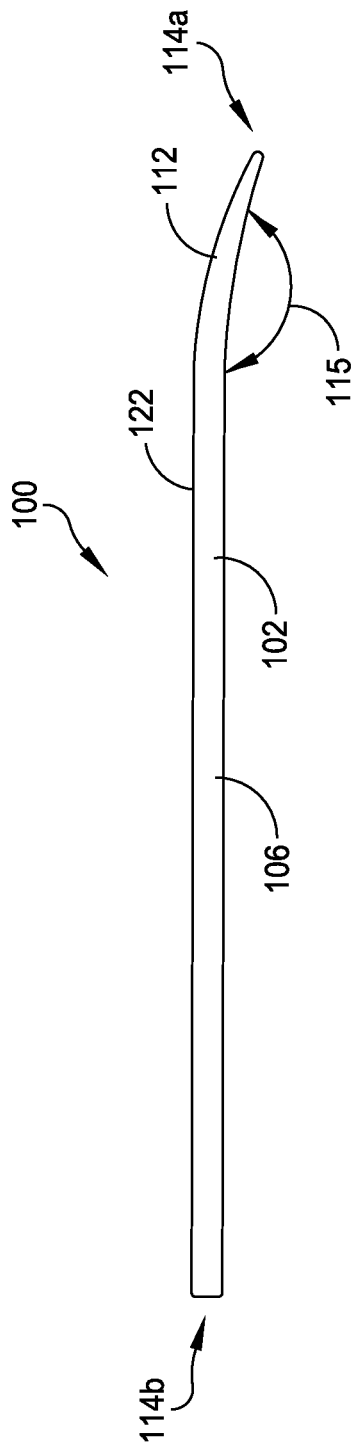
FIG. 2 illustrates a side view of the MIS displacement translator of FIG. 1, in accordance with some embodiments.
Figure 4:
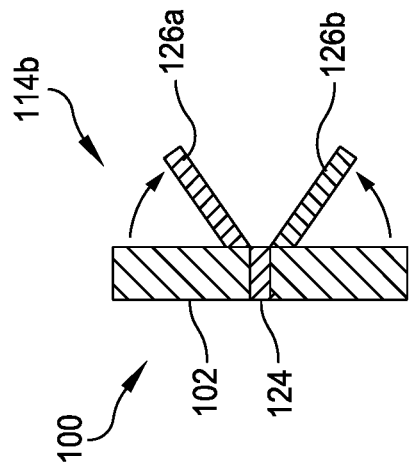
FIG. 4 illustrates a rear view of the MIS displacement translator of FIG. 1 in a deployed position, in accordance with some embodiments.
Figure 3:
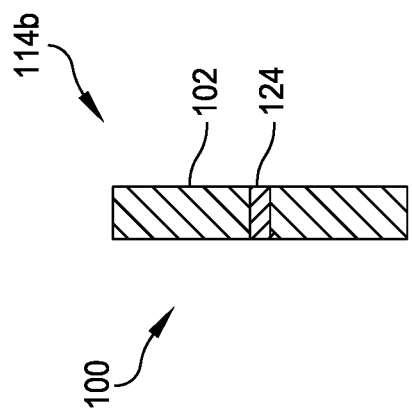
FIG. 3 illustrates a rear view of the MIS displacement translator of FIG. 1 in a collapsed position, in accordance with some embodiments.

In some embodiments, the integrated block 120 can be transitioned from a first, collapsed, position (as illustrated in FIGS. 2 & 3) to a second, deployed, position (as illustrated in FIG. 4). In the collapsed position, the integrated block 120 is co-planar with a surface 122 of the body 102. The integrated block 120 may be positioned partially and/or entirely within the cavity 104 defined by the body 102 in a collapsed position. The integrated block 120 may be transitioned from the collapsed position to a deployed position in which at least a portion of the integrated block 120 is positioned outside of (e.g., is not coplanar with) the body 102.

In some embodiments, the integrated block 120 includes a rod 124 and a plurality of retention elements 126a, 126b configured to pivot about the rod 124. In the illustrated embodiment, the retention elements 126a, 126b are generally rectangular shaped, although it will be appreciated that the retention elements 126a, 126b can include any suitable shape (and may each have a different shape) configured to retain an anatomical feature of a patient. The retention elements 126a, 126b are pivotably coupled to the rod 124 to allow the retention elements 126a, 126b to rotate between a position in-plane with the body 102 (illustrated in FIG. 3) and a position out-of-plane with respect to the body 102 (illustrated in FIG. 4).

In some embodiments, the integrated block 120 includes one or more mechanisms to allow partial deployment, incremental deployment, and/or to resist collapsing once deployed. The mechanism may include any suitable mechanism such as, for example, a ratcheting mechanism, mechanical stops, and/or any other suitable mechanism. The mechanism may be part of and/or formed integrally with the rod 124, one or more retention elements 126a, 126b, the body 102, and/or any other suitable element.

In the illustrated embodiment, the integrated block 120 is a V-block having a first retention element 126a and a second retention element 126b configured to form a V, or wedge, shape when in a deployed position (see FIG. 4). The V-block is configured to retain an anatomical feature, such as a portion of a patient's toe, in a predetermined position. For example, in some embodiments, a distal portion of a toe may be displaced after forming an osteotomy (using, for example, the displacement tip 112 as discussed above). After displacement, the distal portion of the toe is manually rotated and the integrated block 120 is deployed against the distal portion of the toe. The V-shape formed by the first and second retention elements 126a, 126b maintains the distal portion of the toe in the rotated position. After completing a surgical procedure, the anatomical feature may be removed and the integrated block 120 may be transitioned from the deployed position to the collapsed position. In some embodiments, the surface 128a, 128b of each of the retention elements 126a, 126b may include a coating to increase friction and/or otherwise retain the anatomical feature in a fixed position with respect to the retention elements 126a, 126b.

FIGS. 5-8 illustrate a targeting guide 200 including a rotatable arm 230 and a translatable arm 250, in accordance with some embodiments. The targeting guide 200 includes a body 202 extending from a first end 204a to a second end 204b generally along a longitudinal axis 206. The body 202 includes an upper surface 208a, a lower surface 208b, a first side surface 210a, and a second side surface 210b. In some embodiments, the body 202 includes one or more openings 212 (or cavities) extending from any one surface to any other surface. For example, in the illustrated embodiment, an opening 212 extends from a first side surface 210a to a second side surface 210b. The openings 212 may be configured to provide visual alignment indicators, reduce weight of the targeting guide 200, allow a user to grip the targeting guide 200, and/or provide any other suitable function. In some embodiments, the body 202 includes an offset or angled portion 203 adjacent to the first end 204a. The angled portion 203 extends from the body 202 at an angle with respect to the longitudinal axis 206.

The body 202 defines at least one guide hole 214 extending from a first surface to a second surface of the body 202. For example, in the illustrated embodiment, the body 202 includes a first guide hole 214 extending from a first end 204a through the angled portion 203 of the body 202 and exiting from the first side surface 208a. The first guide hole 214 extends on an axis at an angle to the longitudinal axis 206. For example, in the illustrated embodiment, the guide hole 214 extends through the angled portion such that the angled portion 203 and the guide hole 214 are longitudinally aligned, although it will be appreciated that the guide hole 214 can extend through the angled portion 203 at any suitable angle with respect to the longitudinal axis 206. The guide hole 214 is sized and configured to receive a guide element, such as a k-wire 50b, therethrough. The guide hole 214 positions the received guide element at a predetermined angle with respect to the longitudinal axis 206 of the body 202 and at a predetermined location with respect to one or more additional guide elements, as discussed below.

In some embodiments, a rotation housing 216 is coupled to and/or formed integrally with a second end 204b of the body 202. The rotation housing 216 defines a hinge opening 218 sized and configured to receive a first end 234a of a rotatable arm 230 therein. The rotation housing 216 further defines an pin channel 220 sized and configured to receive a pin 224 therein. In some embodiments, the pin 224 defines a guide hole 226 sized and configured to receive a fixation element, such as an olive wire 225, therethrough.

In some embodiments, a rotatable arm 230 is coupled to the rotation housing 216. The rotatable arm 230 includes a body 232 extending between a first end 234a and a second end 234b. The first end 234a of the rotatable arm 230 defines a portion of the pin channel therethrough 220. The pin 224 is inserted through the pin channel 220 to rotatably couple the rotatable arm 230 to the body 202.

The rotatable arm 230 can be rotated about an axis 238 defined by the pin 224 and the pin channel 220. In the illustrated embodiment, the axis 238 defined by the pin 224 and the pin channel 220 is perpendicular to the longitudinal axis 206, although it will be appreciated that the axis 238 may disposed at any angle with respect to the longitudinal axis 206. The rotatable arm 230 may be rotatable within a predetermined range. For example, in the illustrated embodiment, the rotatable arm 230 is rotatable within a 180° range extending from 90° above the longitudinal axis 206 (e.g., +90°) to 90° below the longitudinal axis 206 (e.g., −90°. Although specific embodiments are discussed herein, it will be appreciated that the rotatable arm 230 may have any suitable range of motion, such as, for example, ±90°, ±60°, ±45°, ±30°, and/or any other suitable range.

The second end 234b of the rotatable arm 230 defines an arm channel 240 sized and configured to receive a translatable arm 250 therein. The arm channel 240 is spaced a predetermined distance from the pin channel 220 as determined by the length of the body 232. The arm channel 240 extends through the rotatable arm 230 on a longitudinal axis 242. In the illustrated embodiment, the axis 242 is parallel to the axis 238 and perpendicular to the axis 206, although it will be appreciated that the axis 242 can be disposed at any angle with respect to the axis 206 and/or the axis 238.

In some embodiments, the translatable arm 250 is sized and configured to be received at least partially within the arm channel 240. The translatable arm 250 includes a body 252 extending from a first end 254a to a second end 254b on the axis 242. In the illustrated embodiment, the body 252 includes a generally rectangular shape defined by an upper surface 256a, a lower surface 256b, and a perimeter wall 258, although it will be appreciated that the translatable arm 250 can include any suitable shape, such as rectangular, cylindrical, etc.

The translatable arm 250 is moveable on the axis 242. The translatable arm 250 is maintained parallel with the rotatable housing 216 by the arm channel 240. Translation of the translatable arm 250 within the arm channel 240 alters a distance between a guide portion 260 positioned at a first end 254a of the translatable arm 250 and a fixed lateral position, such as, for example, the rotatable arm 230 (e.g., an axis defined by the rotatable arm 230). In use, a first guide element, such as a first k-wire 50a or guide sleeve (not shown) is inserted through the guide portion 260 to visualize an insertion trajectory of a second guide element, such as a second k-wire 50b or guide sleeve 52 inserted through the guide hole 214 defined through the body 202 (see FIG. 8). Before, during, and/or after insertion of the first guide element 50a, the translatable arm 250 may be translated within the arm channel 240 to position the first guide element 50a to match and/or otherwise provide visualization of the trajectory of the second guide element 50b.

In some embodiments, the guide portion 260 includes a rotation body 262 and a rotatable guide element 264. The rotation body 262 defines a rotation channel 266 sized and configured to receive a rotatable guide pin 268 therein. In the illustrated embodiment, the rotation body 262 defines a cylindrical shape, although it will be appreciated the rotation body 262 can define any suitable shape, such as, for example, a rectangular shape, a cylindrical shape, an irregular shape, etc. In some embodiments, the rotation body 262 is sized and configured to prevent the translatable arm 250 from translating fully through the arm channel 240 in a first direction. For example, in the illustrated embodiment, the rotation body 262 has both a height and a radius that prevent the rotation body 262 from moving through the arm channel 240, although it will be appreciated that a single dimension (e.g., only height or only radius) is sufficient to prevent movement of the guide portion 260 through the arm channel 240.

In some embodiments, the rotatable guide element 264 is coupled to the rotation body 262. The rotatable guide element 264 includes a rotatable pin 268 and a fixed cap 270. The rotatable pin 268 is received within the rotation channel 266 defined by the rotation body 262. The rotatable pin 268 defines at least one guide hole 272 extending through the body of the rotatable pin 268. In the illustrated embodiment, the at least one guide hole 272 is centered with respect to a diameter of the pin 268, although it will be appreciated one or more guide holes 272 may be offset within the pin 268.

In some embodiments, the fixed cap 270 is fixedly coupled to the rotation body 262. The fixed cap 270 defines a guide channel 274 sized and configured to receive a first guide element 50a therein and to limit rotation of the first guide element 50a. For example, in the illustrated embodiment, the guide channel 274 includes a closed channel having a channel wall 276 blocking a portion of the guide channel 274 and preventing complete rotation of the guide element 50a inserted through the guide hole 272 of the rotatable pin 268. The guide channel 274 allows rotation of the guide element 50a within a predetermine range, such as, for example, 0-270°, 0-180°, 0-90°, etc. As discussed in greater detail below, in some embodiments, the guide portion 260 includes a fixed guide portion.

Figure 5:
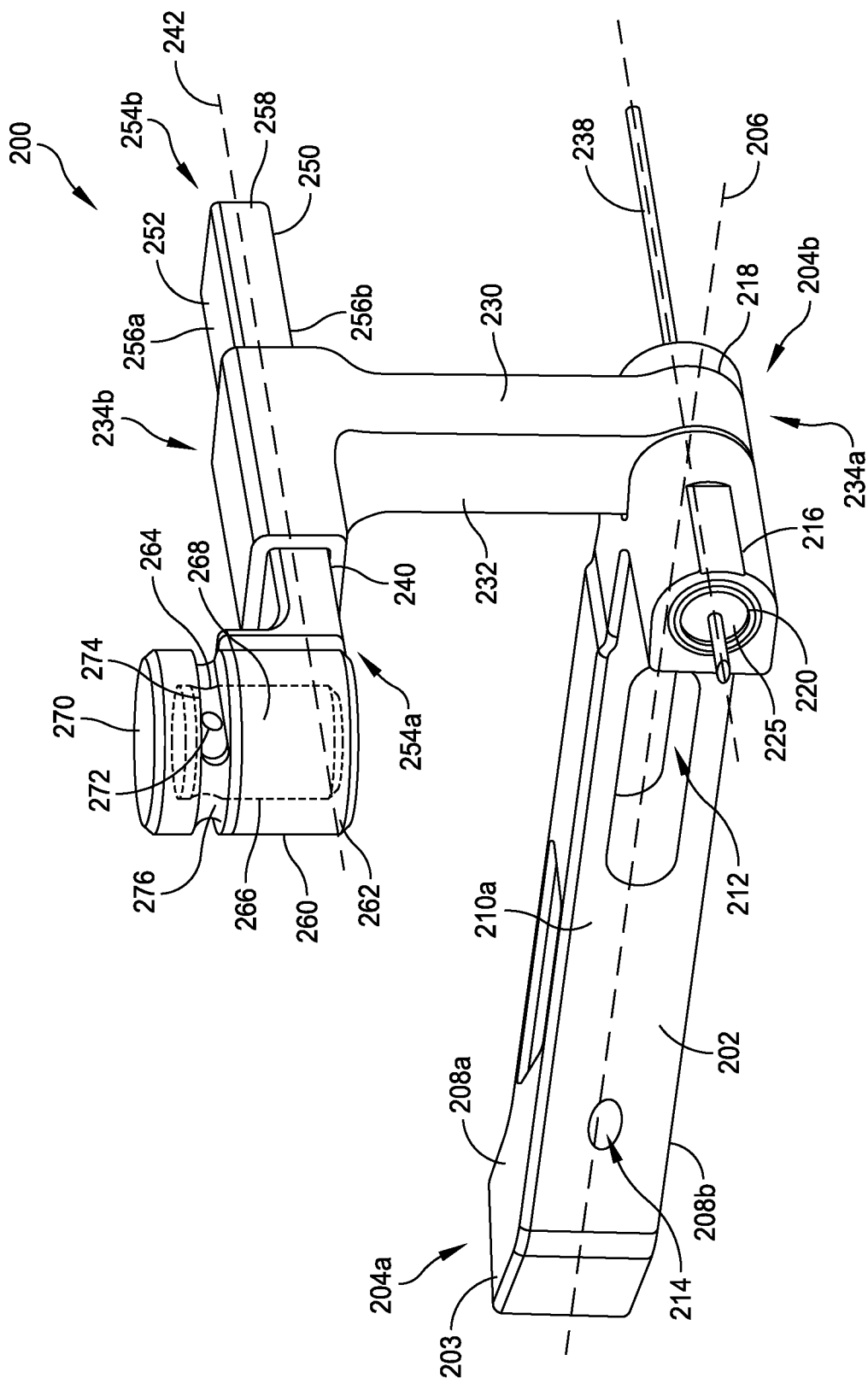
FIG. 5 illustrates an isometric view of a first side of a k-wire guide including a translatable arm and a rotatable arm, in accordance with some embodiments.
Figure 6:
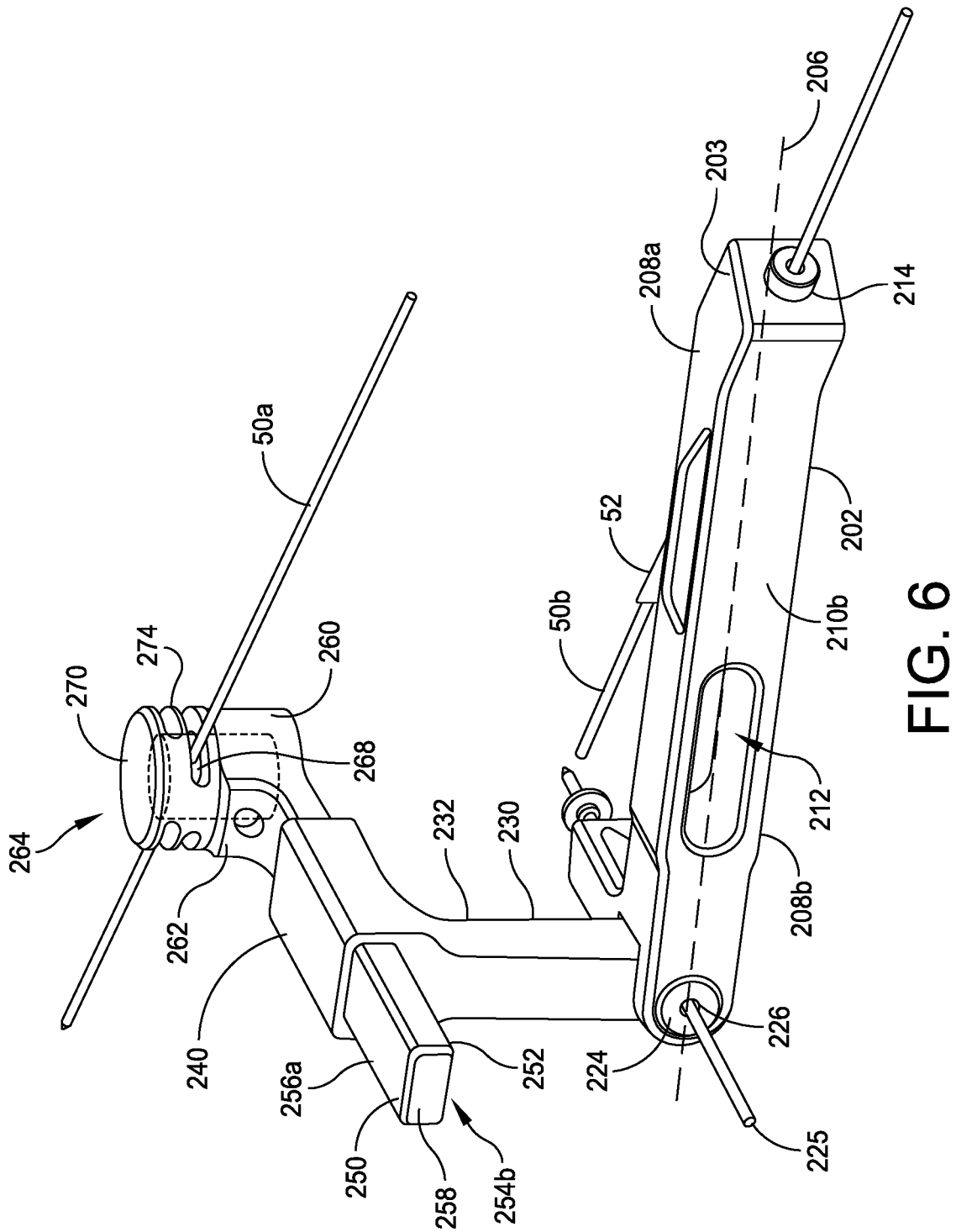
FIG. 6 illustrates an isometric view of a second side of the k-wire guide of FIG. 4, in accordance with some embodiments.
Figure 7:
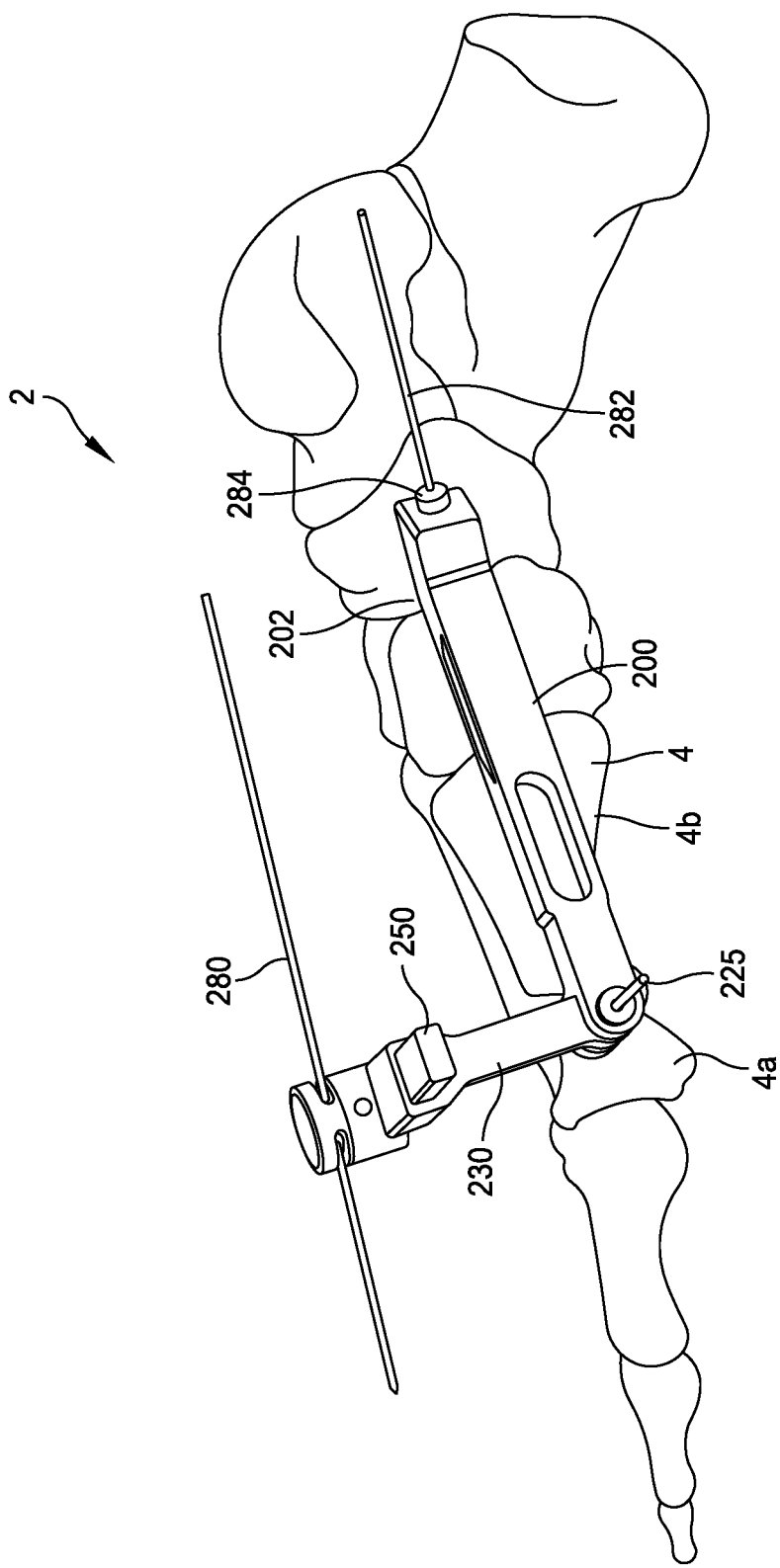
FIG. 7 illustrates the k-wire guide of FIG. 5 positioned adjacent to a foot, in accordance with some embodiments.

FIG. 7 illustrates the targeting guide 200 of FIGS. 5-6 positioned adjacent to a foot 2, in accordance with some embodiments. In use, the targeting guide 200 is positioned adjacent to at least one bone 4 of a foot 2, such as, for example, a first metatarsal. The bone 4 may have an osteotomy formed therein prior to and/or after positioning the targeting guide 200 adjacent to the bone 4. The axis 206 of the body 202 is aligned with an axis of the bone 4. A pin driver (not shown) may be used to drive a tip of the olive wire 225 (or other fixation element) into a portion of the bone 4, such as a first portion 4a. In the illustrated embodiment, the first portion 4a includes a head of the first metatarsal.

Figure 8:
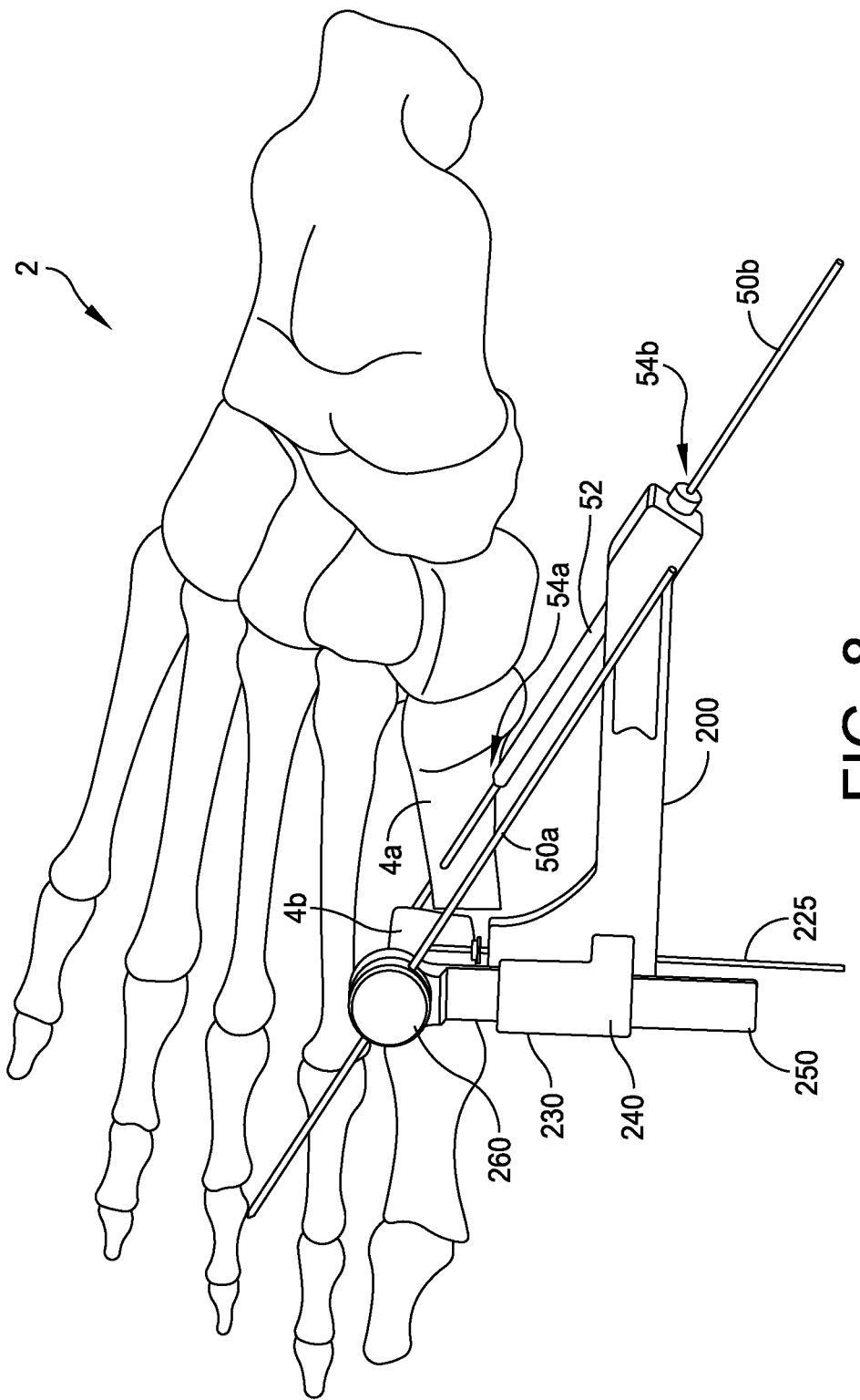
FIG. 8 illustrates the k-wire guide of FIG. 7 having at least one k-wire inserted through a guide hole and into a portion of a foot, in accordance with some embodiments.

A first guide element 50a is inserted through the guide hole 272 defined in the rotatable pin 268. The first guide element 50a and the rotatable pin 268 may be rotated to align a long axis of the guide element 50a parallel to an axis of a guide hole 214 formed through the body 202. After aligning the axes, the translatable arm 250 is translated within the arm channel 240 to position the first guide element 50a in a position configured to provide visualization for insertion of a second guide element 50b into the bone 4, as shown in FIG. 8. The guide element 50a may be aligned with respect to a predetermined plane, such as, for example, the anterior-posterior (A-P) plane.

In some embodiments, after positioning the first guide element 50a, a guide sleeve 52 is inserted through the guide hole 214 and a second guide element 50b is inserted into the first bone 4 through the guide sleeve 52. The guide sleeve 52 may include a first end 54a positioned in contact with and/or immediately adjacent to a second bone portion 4b of the first bone 4. The guide sleeve 52 defines a longitudinal channel extending from the first end 54a to a second end 54b. The longitudinal channel is sized and configured to receive the second guide element 50b therethrough. The second guide element 50b is guided into contact with the second bone portion 4b by the guide sleeve 52 and advanced through the second bone portion 4b into the first bone portion 4a to fix the location of the first bone portion 4a relative to the second bone portion 4b. After inserting the second guide element 50b, the guide sleeve 52 and the targeting guide 200 are removed from the foot 2, leaving the second guide element 50b in place for further guidance of drilling, fixation, and/or other procedures.

Figure 9:
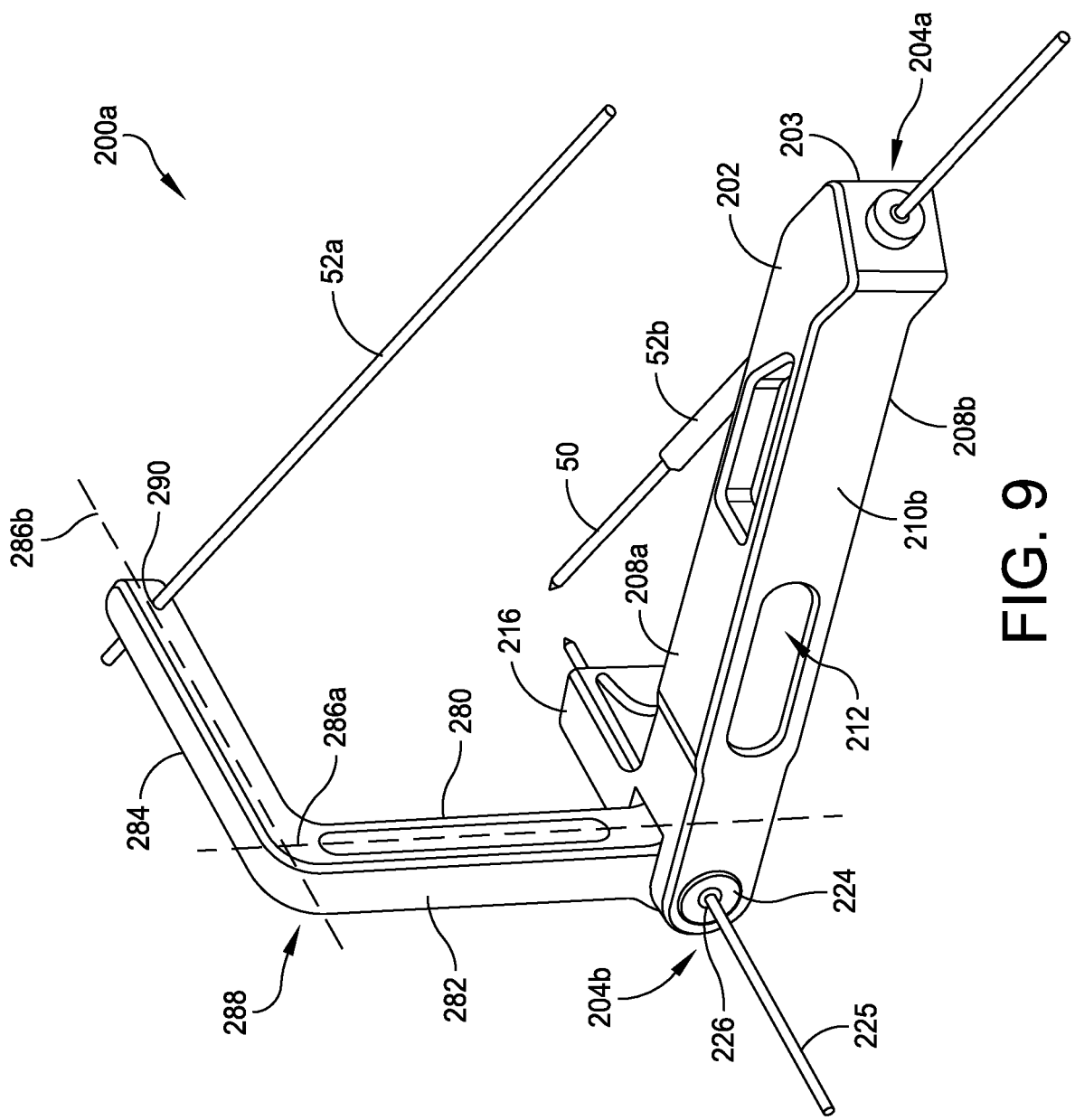
FIG. 9 illustrates an isometric view of a k-wire guide including a single-piece arm, in accordance with some embodiments.

FIG. 9 illustrates one embodiment of a targeting guide 200a having a rotatable guide arm 280, in accordance with some embodiments. The targeting guide 200a is similar to the targeting guide 200 discussed above, and similar description is not repeated herein. The targeting guide 200a includes a rotatable guide arm 280 in place of the rotatable arm 230 and translatable arm 250 of the targeting guide 200. The rotatable guide arm 280 is rotatable coupled to the body 202 by a pin 224 at a first end 288a as discussed above with respect to the targeting guide 200. The rotatable guide arm 280 includes a first portion 282 extending substantially along a first longitudinal axis 286a and a second portion 284 extending substantially along a second longitudinal axis 286b from a second end 288b of the first portion 282. In some embodiments, the second portion 284 is disposed in a common plane but perpendicular to the first portion 282, as illustrated in FIG. 9, although it will be appreciated that the first portion 282 and the second portion 284 may be disposed at any suitable angle, in plane and/or out of plane.

The second portion 284 of the rotatable guide arm 280 defines a guide hole 290 extending therethrough. The guide hole 290 is sized and configured to receive a guide element, such as a guide wire 50a, therethrough. The guide hole 290 includes a hole axis extending parallel to an axis defined by the guide hole 214 formed in the body 202. The guide hole 290 may be configured to position a guide element, such as guide wire 50a, in-plane or out-of-plane with respect to a guide element, such as guide wire 50b, inserted through the guide hole 214 formed in the body 202. The guide element, e.g., guide wire 50a, inserted through the guide hole 290 may be removably inserted into the guide hole 290 and/or may be fixedly coupled to the second portion 284, such as, for example, by an adhesive, welding, and/or any other suitable fixation. Although embodiments are discussed herein including a guide wire 50a, it will be appreciated that any suitable guide element, such as a guide sleeve, guide wire, k-wire, etc., may be used.

Figure 10:
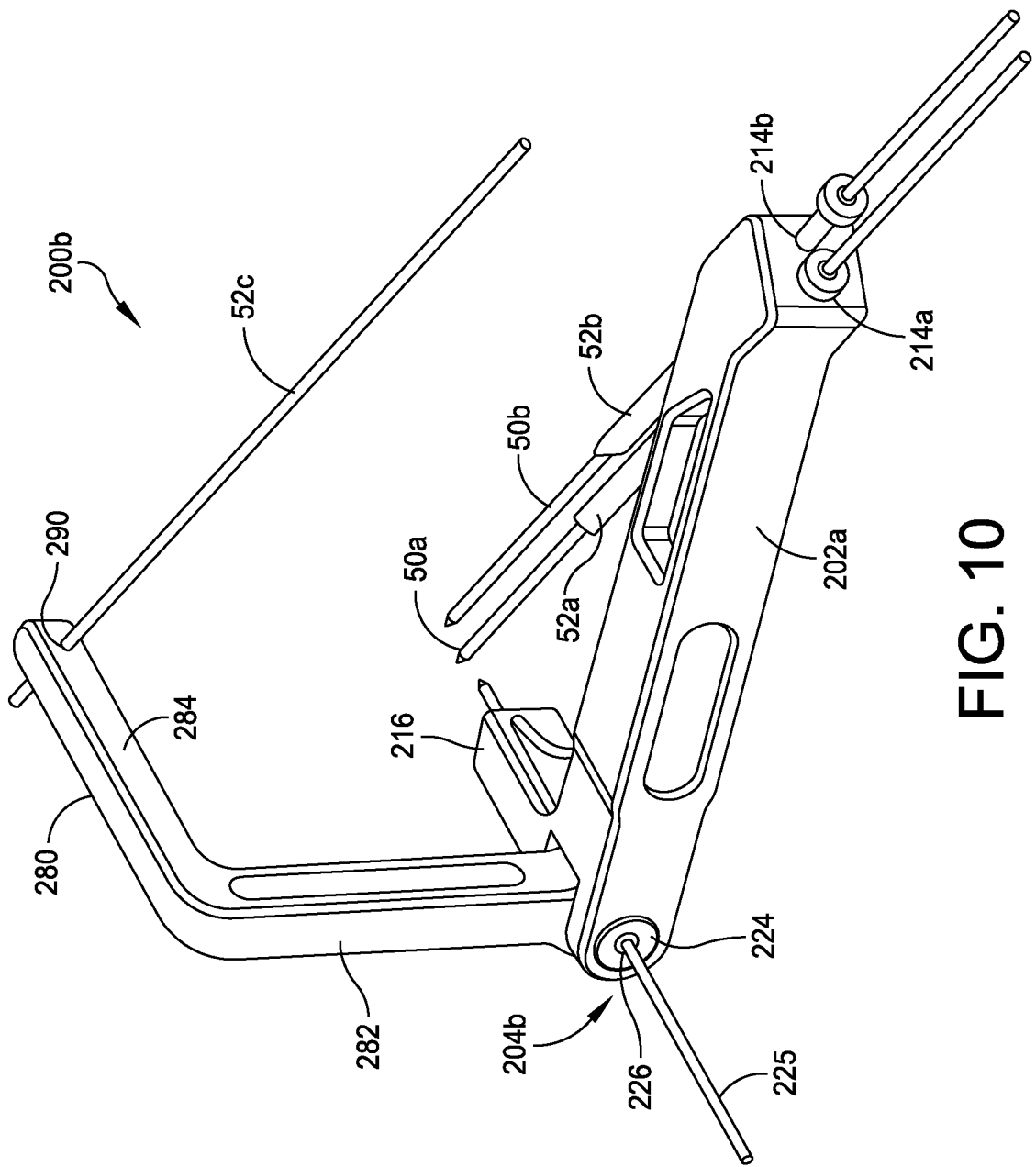
FIG. 10 illustrates an isometric view of a k-wire guide including a single-piece arm and a plurality of guide holes formed through the body, in accordance with some embodiments.

In some embodiments, the targeting guide 200, 200a can include multiple guide holes 214 formed through the body 202. For example, FIG. 10 illustrates one embodiment of a targeting guide 200b including a first guide hole 214a and a second guide hole 214b formed through the body 202a. The targeting guide 200b is similar to the targeting guide 200a discussed above, and similar description is not repeated herein. The first guide hole 214a and the second guide hole 214b extend through the body 202a on parallel hole axes that are aligned in-plane with respect to a plane defined by the longitudinal axis 206 of the body 202a and the axes of the guide holes 214a, 214b, although it will be appreciated that one or both of the guide holes 214a, 214b can be positioned out-of-plane and/or the guide holes 214a, 214b may be non-parallel.

In some embodiments, one or more elements of the displacement elevator 100 and one or more elements of a targeting guide 200, 200a, 200b may be combined into a single combination displacement and targeting device. For example, in some embodiments, a combination displacement and targeting device including a displacement tip configured to displace a bone fragment and a targeting guide configured to guide insertion of at least one guide or fixation element may be used to prevent switching of surgical devices during surgery.

Figure 11:
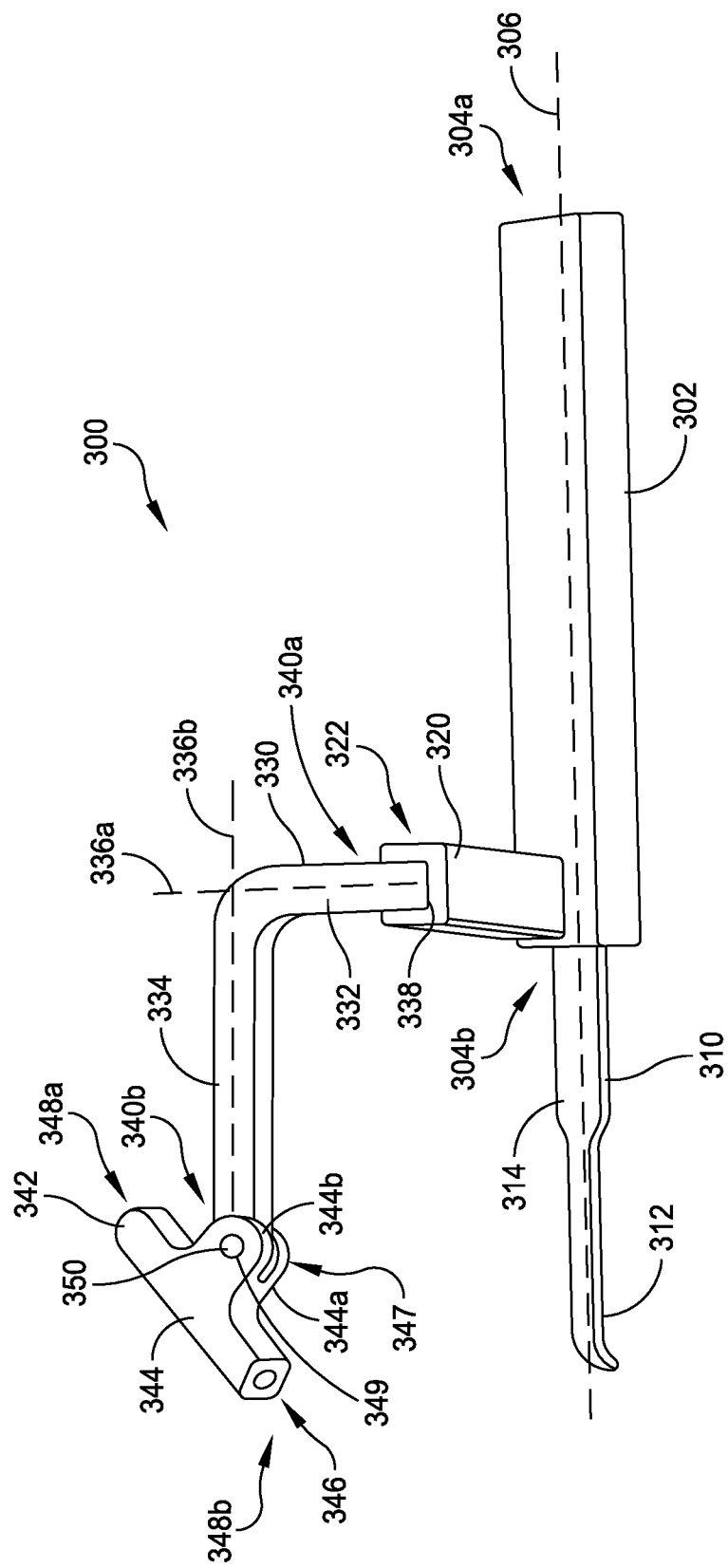
FIG. 11 illustrates a MIS integrated displacement translator and targeting arm, in accordance with some embodiments.

FIG. 11 illustrates a combination displacement and targeting surgical tool 300, in accordance with some embodiments. The combination displacement and targeting surgical tool 300 includes a handle body 302 extending substantially along a longitudinal axis 306 from a first end 304a to a second end 304b. In the illustrated embodiment, the handle body 302 has a generally rectangular shape, although it will be appreciated that the handle body 302 can have any suitable shape, such as, for example, a rectangular, cylindrical, irregular, etc. A displacement extension 310 extends from a second end 304b of the body 302. The displacement extension 310 includes a longitudinal body 314 extending substantially along the longitudinal axis 306 and a displacement tip 312. The displacement tip 312 is similar to the displacement tip 112 discussed above, and similar description is not repeated herein.

In some embodiments, the displacement and targeting surgical tool 300 includes an arm extension 320 extending from the body 302. In the illustrated embodiment, the arm extension 320 extends perpendicular to the longitudinal axis 306, although it will be appreciated that the arm extension 320 can extend at any suitable angle with respect to the body 302 and/or the longitudinal axis 306. The arm extension 320 is coupled to targeting arm 330 at a first end 322. The targeting arm 330 may be pivotably coupled to the arm extension 320 by a pivoting connection 338 and/or may be fixedly coupled to the targeting arm 330.

In some embodiments, the targeting arm 330 includes a first portion 332 extending substantially on a first arm axis 336a and a second portion 334 extending substantially on a second arm axis 336b. The first arm axis 336a is disposed at a predetermined angle with respect to the second arm axis 336b. For example, in the illustrated embodiment, the first arm axis 336a is positioned perpendicular (e.g., 90°) to the second arm axis 336b, although it will be appreciated that a greater and/or lesser angle is possible.

In some embodiments, the targeting arm 330 may be adjustable along one or more of the first arm axis 336a and the second arm axis 336b. For example, in some embodiments, the targeting arm 330 may be lengthened and/or shortened along the first arm axis 336b to adjust the distance between the handle body 302 and the targeting arm 330. In other embodiments, the arm extension 320 may be adjustable to adjust the distance between the handle body 302 and the targeting arm 330. Although specific embodiments are discussed herein, it will be appreciated that the first portion 332 and/or the second portion 334 of the targeting arm and/or the targeting extension 320 may be shortened and/or lengthened to adjust a position of the pivotable targeting head 342 with respect to the body 302.

Figure 12:
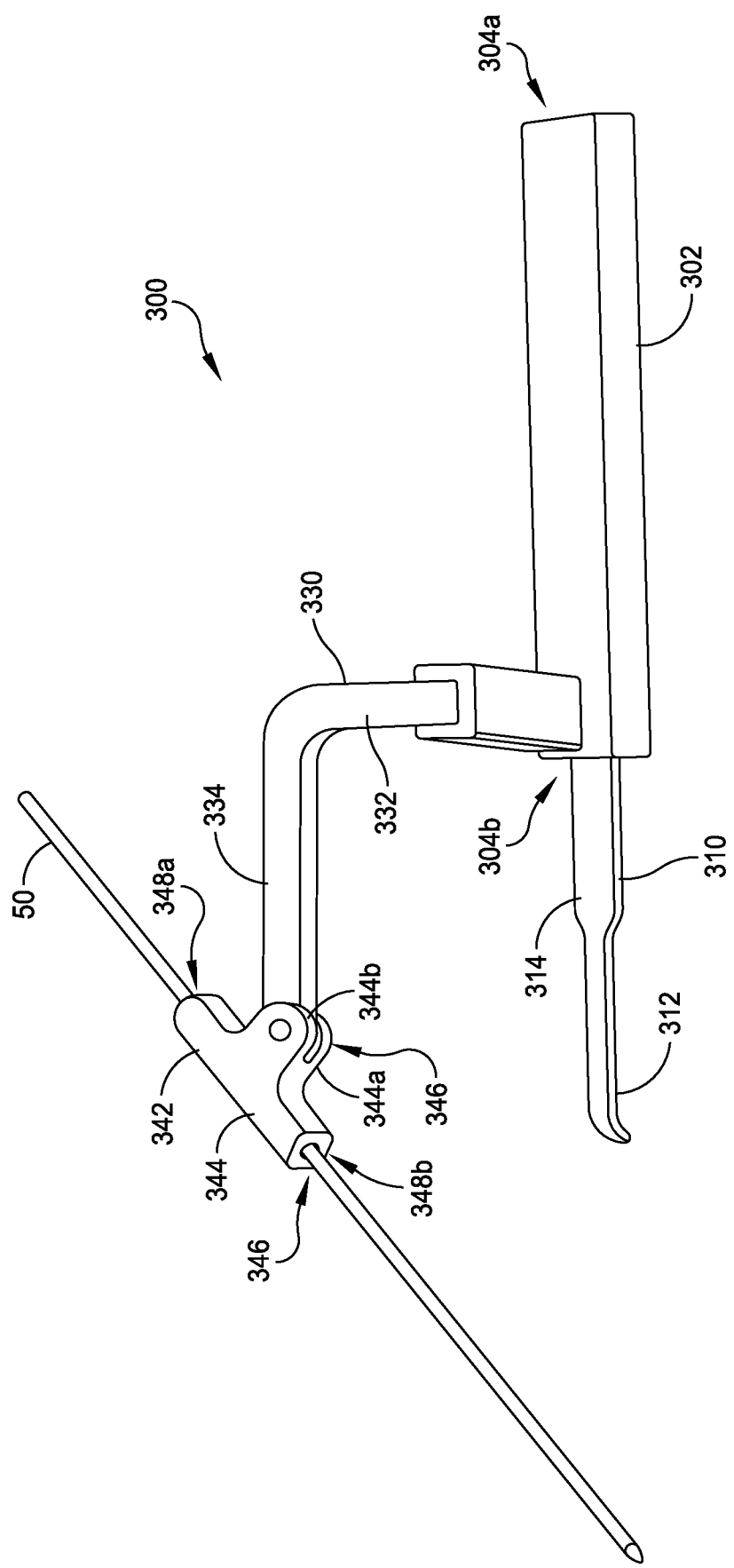
FIG. 12 illustrates the MIS integrated displacement translator and targeting arm of FIG. 11 including a k-wire inserted through a targeting head of the targeting arm, in accordance with some embodiments.

In some embodiments, a pivoting targeting head 342 is coupled to a second end 340b of the targeting arm 330. The pivoting targeting head 342 includes a targeting body 344 defining at least one guide hole 346 extending from a first side 348a to a second side 348b. The guide hole 346 is sized and configured to receive a guide element, such as a k-wire or guide sleeve, therethrough, as illustrated in FIG. 12. In some embodiments, the body 344 includes a first hinge element 344a and a second hinge element 344b defining an arm receiving slot 347 therebetween. The arm receiving slot 347 is sized and configured to receive a second end 340b of the targeting arm 330 therein. At least one of the hinge elements 344a, 344b and the second end 340b of the targeting arm 330 define a pin slot 349 sized and configured to receive a pivot pin 350 therein. The pivot pin 350 pivotably couples the targeting head 342 to the targeting arm 330.

In some embodiments, the combination displacement and targeting surgical tool 300 includes a modular design allowing one or more of the components to be connected and/or disconnected from one or more other components. For example, in some embodiments, the displacement extension 310 is slideably received within a channel defined in the front of the handle body 302 such that the displacement extension 310 may be used separately from the handle body 302. As another example, the targeting arm 330 may be configured to be connected/disconnected to the arm extension 320. Although specific embodiments are discussed herein, it will be appreciated that any suitable portion of the combination displacement and targeting surgical tool 300 can include a modular configuration.

In use, a surgeon creates an incision in the skin adjacent to a first bone, such as the first metatarsal illustrated in FIG. 9. An osteotomy is generated in the first bone, for example, using a burr. The displacement tip 312 of the displacement extension 310 is inserted into the medullary canal of a first portion of the bone, such as, for example, a proximal fragment of a first metatarsal. The displacement extensions 310 and/or the handle body 302 are rotated (or pivoted) about the displacement tip 312 to displace a second portion (e.g., a distal fragment of the first metatarsal laterally.

A guide element, such as a k-wire 50 as illustrated in FIG. 12, is inserted through the rotatable targeting head 342. The targeting head 342 and/or the targeting arm 330 are adjusted to position the guide element, e.g., k-wire 50, at a position matching an intended trajectory of a guide element inserted into the first bone. The surgical site may be reviewed visually (e.g., fluoroscopically) to confirm position of the k-wire 50 and/or to mark an insertion path. A k-wire or other fixation device is inserted into a surgical wire driver and inserted along a trajectory parallel to the trajectory of the guide element 50. After inserting the k-wire through the first bone portion and the second bone portion, the combination displacement and targeting surgical tool 300 can be removed from the surgical site and additional surgical procedures (e.g., insertion of additional guide elements, fixation, etc.) can be performed.

Figure 13:
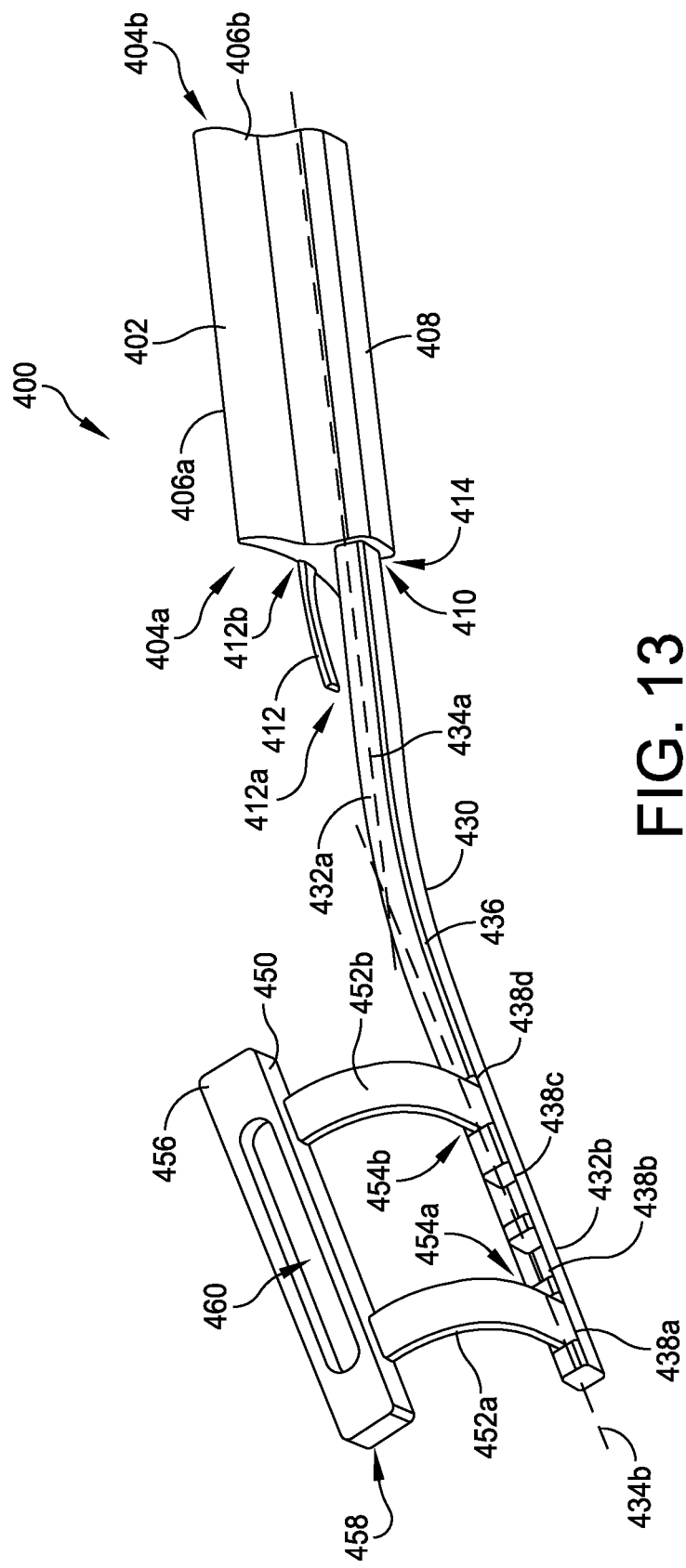
FIG. 13 illustrates an MIS combination displacement translator and targeting arm, in accordance with some embodiments.

FIG. 13 illustrates a combination displacement and targeting surgical tool 400, in accordance with some embodiments. The combination displacement and targeting surgical tool 400 includes a handle body 402 extending from a first end 404a to a second end 404b. The handle body 402 includes a thickness extending between a first surface 406a and a second surface 406b. In some embodiments, an arm channel extension 408 is coupled to and/or formed integrally with the second surface 406a of the body 402. The arm channel extension 408 defines a channel 410 sized and configured to receive a targeting arm 430 therein, as discussed in greater detail below. In the illustrated embodiment, the arm channel extension 408 (and the arm channel 410) are centered with respect to the handle body 402, although it will be appreciated that the arm channel extension 408 may be offset with respect to the handle body 402.

In some embodiments a displacement tip 412 extends substantially longitudinally from a first side 404a of the body 402. The displacement tip 412 is similar to the displacement tip 112 discussed above in conjunction with displacement translator 100, and similar description is not repeated herein. The displacement tip 412 may include a curved and/or straight profile. For example, in the illustrated embodiment, the displacement tip 412 defines an arc extending from a first end 412a to a second end 412b of the displacement tip 412.

In some embodiments, the arm channel 410 is sized and configured to receive a portion of a targeting arm 430 therein. The arm channel 410 may define a closed channel (e.g., having an opening at only a first end) or an open channel (e.g., having an opening at either end of the channel 410). The arm channel 410 may extend the entire length of the body 402 (as illustrated) or may extend over only a portion of the body 402. The arm channel 410 defines at least one opening 414 sized and configured to receive a first end of the targeting arm 430 therein.

In some embodiments, the targeting arm 430 includes a first longitudinal portion 432a extending substantially on a first longitudinal axis 434a and a second longitudinal portion 432b extending substantially on a second longitudinal axis 434b disposed at an angle with respect to the first longitudinal axis 434a. A curved portion 436 couples the first longitudinal portion 432a to the second longitudinal portion 432b. The curved portion 436 is configured to position the second longitudinal portion 434b at an angle with respect to the first longitudinal portion 434a to provide visualization with respect to a bone and/or to position a targeting body 450, as discussed in greater detail below. The first longitudinal portion 432a is sized and configured to be received within the arm channel 410. The targeting arm 430 may include one or more bumps, surface slots, markings, and/or other suitable depth marking configured to allow the targeting arm 430 to be inserted into the arm channel 410 at a predetermined depth.

In some embodiments, the targeting arm 430 defines one or more slots 438a-438d sized and configured to receive a portion of a targeting body 450 therein. The one or more slots 438a-438d may be defined through any portion of the targeting arm 430. For example, in the illustrated embodiment, each of the slots 438a-438d are formed through the second longitudinal portion 432b, although it will be appreciated that some or all of the slots 438a-438d may be formed through the first longitudinal portion 432a. In some embodiments, the slots 438a-438d are replaced with another suitable attachment mechanism, such as, for example, snaps, a mechanical joining mechanism, etc. In other embodiments, the slots 438a-438d are omitted and the targeting body 450 is formed integrally with and/or permanently coupled to the targeting arm 430.

In some embodiments, the targeting arm 430 includes one or more radiopaque elements configured to visualize alignment in one or more planes. For example, in some embodiments, the targeting arm 430 is made at least partially of a radiopaque material. As another example, in some embodiments, the targeting arm 430 includes one or more radiopaque strips coupled to and/or embedded in the targeting arm 430. The radiopaque elements may be configured to provide visualization of the alignment between the targeting arm 430 and a bone using fluoroscopy (or other suitable imaging technique).

In some embodiments, a targeting body 450 is releasably coupled to the targeting arm 430. For example, in the illustrated embodiment, the targeting body 450 includes a first coupling leg 452a and a second coupling leg 452b each including a free end 454a, 454b sized and configured to be received at least partially within one of the slots 438a-438d formed in the targeting arm 430. It will be appreciated that the targeting body 450 may include different coupling mechanisms and/or may omit one or more coupling legs 452a, 452b in embodiments having a different coupling mechanism, such as snaps, formed on the targeting arm 430.

In some embodiments, the targeting body 450 includes a targeting body 456 defining one or more guide holes 458 therethrough. The guide holes 458 are sized and configured to receive a guide element, such as a k-wire, therethrough. The guide element is positioned by the guide hole 458 to visualize a trajectory of a guide element inserted into a bone, such as a first metatarsal, as discussed above with respect to targeting guide 200. In some embodiments, the targeting body 456 includes a slot 460 configured to provide a viewing window for alignment.

In some embodiments, the targeting body 456 includes one or more radiopaque elements configured to provide visualization of a trajectory of a guide element inserted into a bone, such as a first metatarsal. For example, in some embodiments, the targeting body 456 (or a portion thereof) is formed of a radiopaque material. As another example, in some embodiments, the targeting body 456 (or a portion thereof) is formed of a radiolucent material having one or more radiopaque stripes (or other elements) embedded therein. Although specific embodiments are discussed herein, it will be appreciated that the targeting body 456 can provide targeting in any suitable spectrum and/or using any suitable mechanism.

Figure 14:
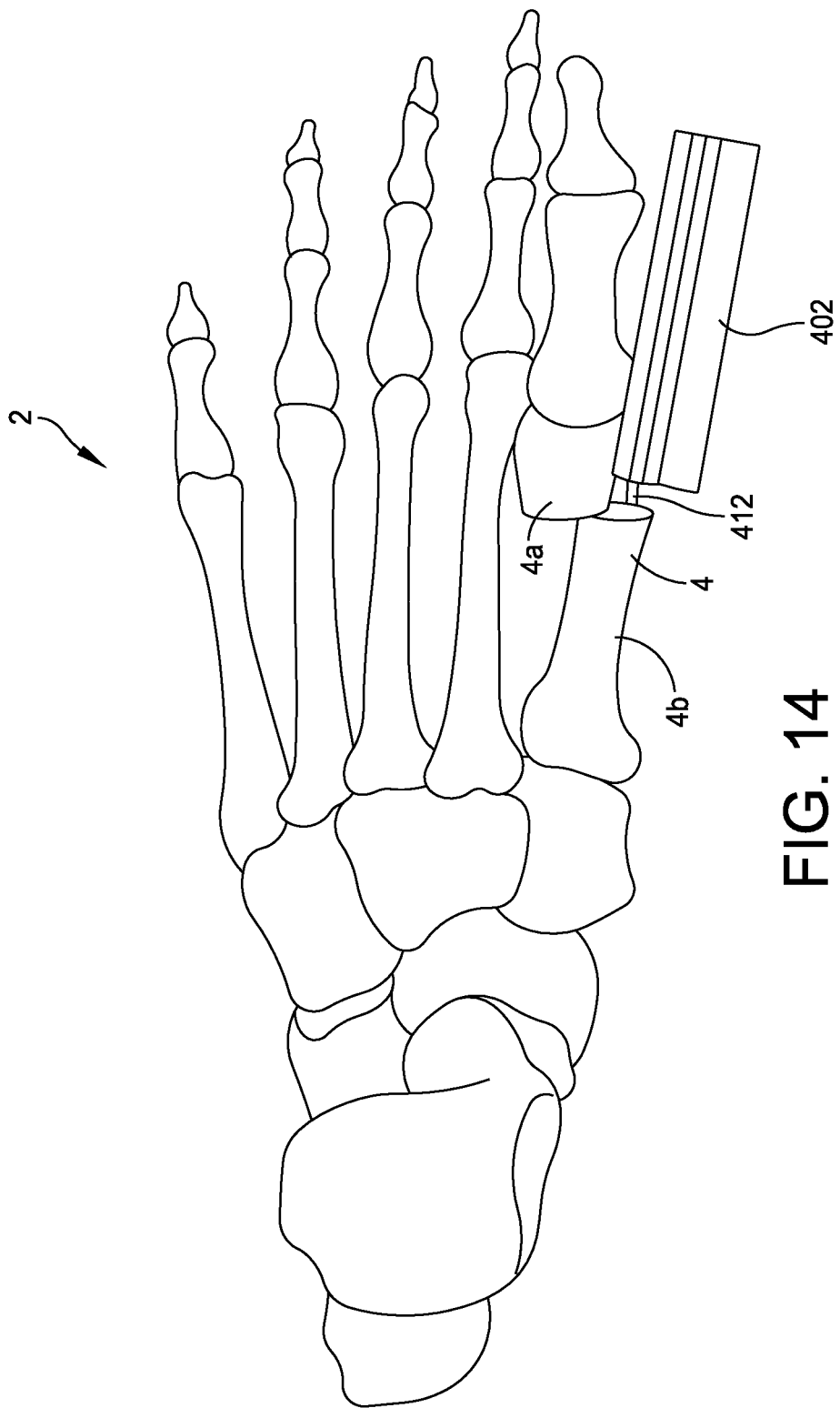
FIG. 14 illustrates a translation body of the MIS combination displacement translator and guide of FIG. 13 positioned adjacent to a foot having an osteotomy formed therein, in accordance with some embodiments.

In use, the combination displacement and targeting surgical tool 400 is configured to provide displacement of a bone fragment and targeting for insertion of one or more guide elements without requiring multiple surgical tools. As illustrated in FIG. 14, after forming an osteotomy in a first bone 4, such as a first metatarsal, the handle body 402 of the combination displacement and targeting surgical tool 400 is positioned adjacent to a second bone fragment 4b. The displacement tip 412 is inserted into a medullary canal of the second bone fragment 4b and the handle body 402 is pivoted to displace the second bone fragment 4b relative to the first bone fragment 4a.

Figure 15:
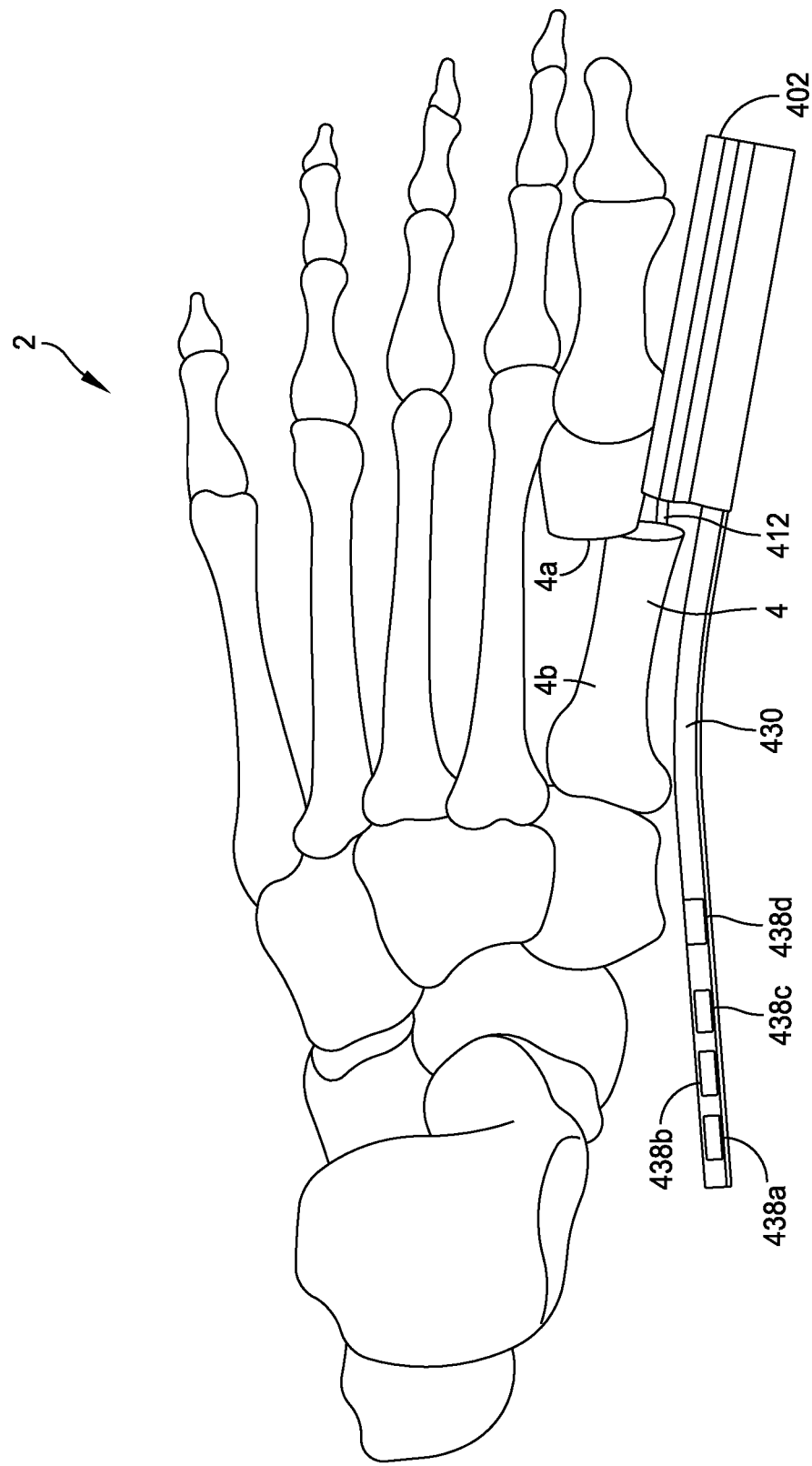
FIG. 15 illustrates the MIS combination displacement translator and guide of FIG. 14 having a targeting arm coupled to the translation body, in accordance with some embodiments.

As shown in FIG. 15, after displacing the second bone fragment 4b, a targeting arm 430 is coupled to the handle body 402, for example, by slideably inserting a portion of the targeting arm 430 into an arm channel 410 defined by the handle body 402 (see FIG. 13). The targeting arm 430 includes a first longitudinal portion 432a extending substantially on a first longitudinal axis 434a shared with the handle body 402 and a second longitudinal portion 432b extending substantially on a second longitudinal axis 434b disposed at an angle with respect to the first longitudinal axis 434a (see FIG. 13).

Figure 16:
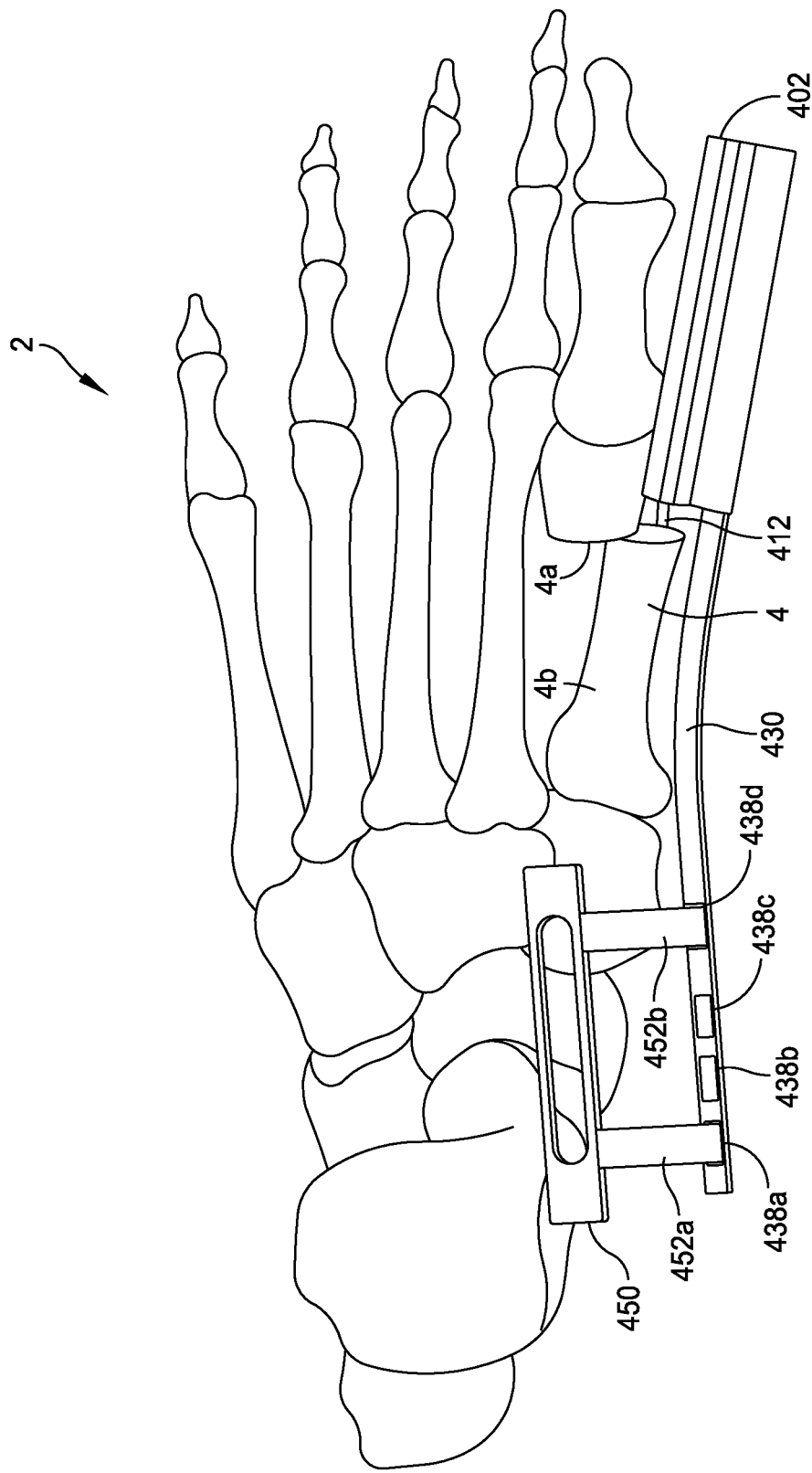
FIG. 16 illustrates the MIS combination displacement translator and guide of FIG. 15 having a k-wire guide coupled to the targeting arm, in accordance with some embodiments.
Figure 17:
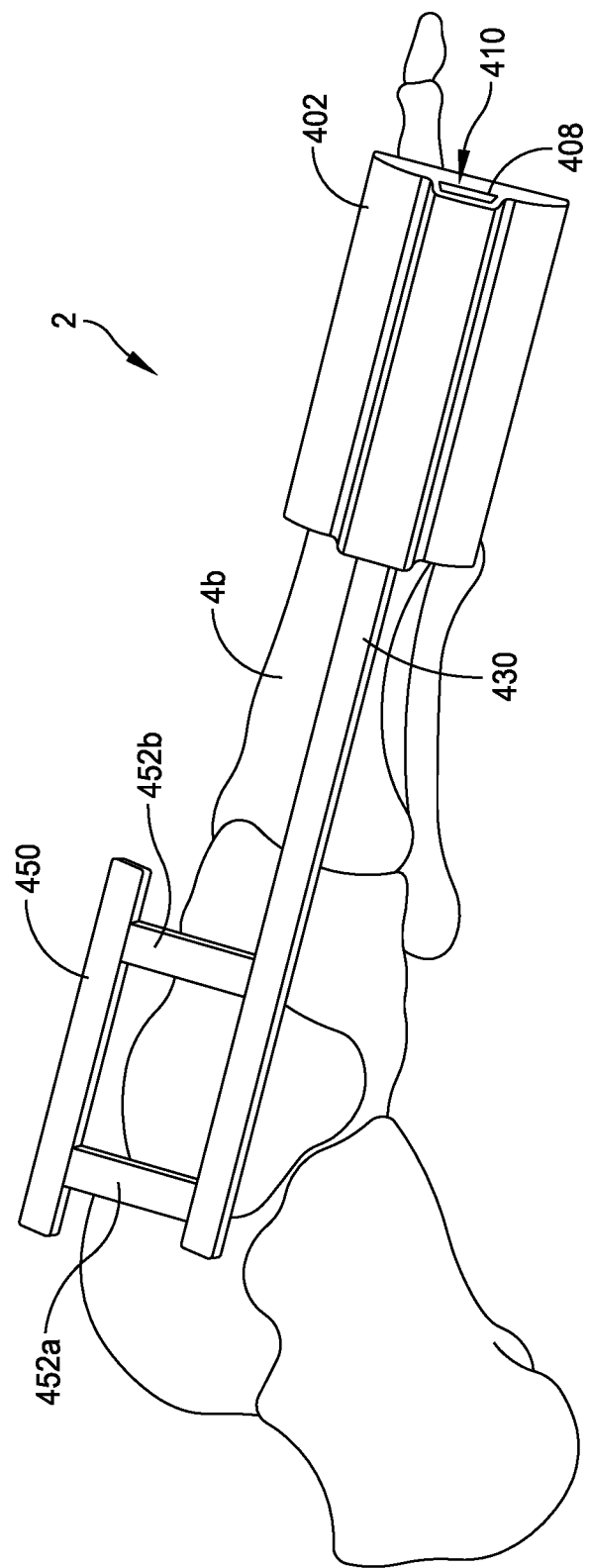
FIG. 17 illustrates a side view of the MIS combination displacement translator and guide of FIG. 16, in accordance with some embodiments.

As shown in FIGS. 16-17, a targeting body 450 is coupled to the targeting arm 430 using a suitable coupling mechanism. For example, in the illustrated embodiment, a first coupling leg 452a and a second coupling leg 452b are slideably inserted into slots 438a, 438d defined by the targeting arm 430, although it will be appreciated that other suitable coupling mechanisms may be used. The targeting body 450 may be used to visualize an insertion trajectory of one or more guide elements. For example, the targeting body 450 may include one or more guide holes for receiving a guide element therethrough and/or may include one or more radiopaque guide elements formed integrally therewith.

Figure 18:
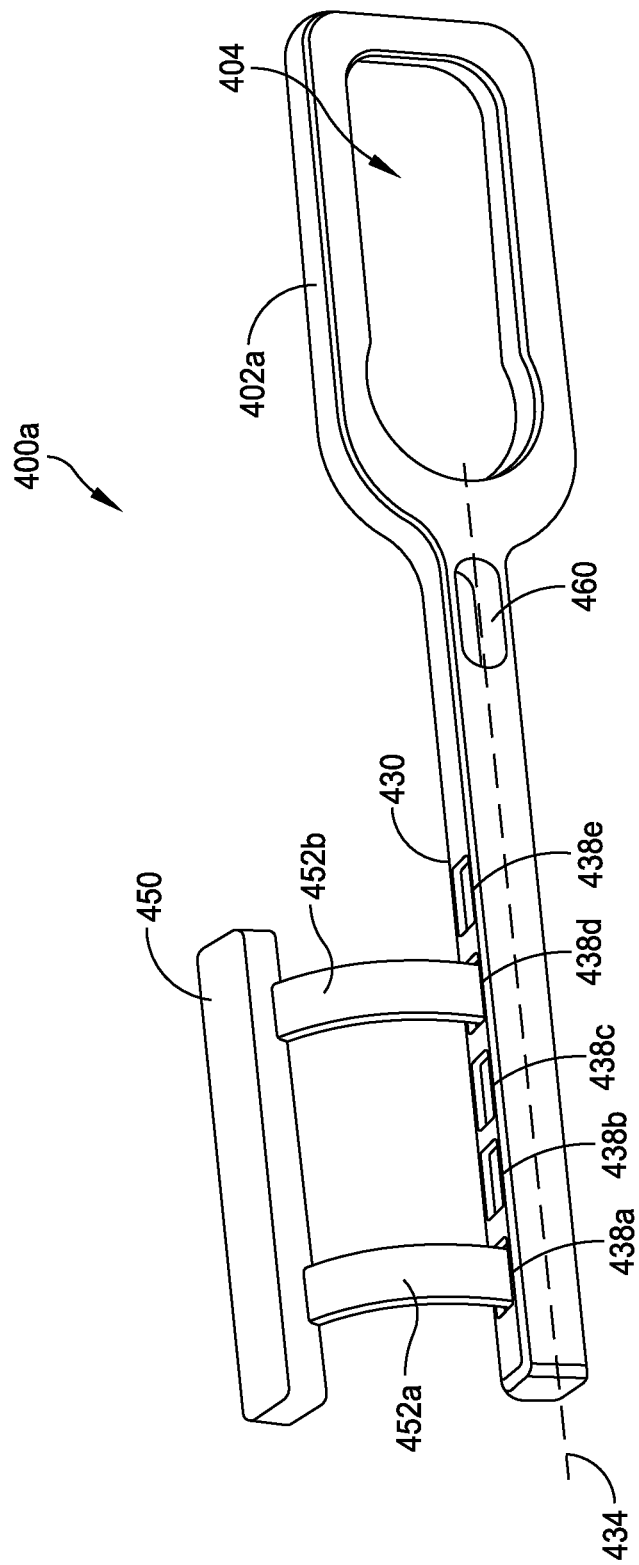
FIG. 18 illustrates an MIS combination displacement translator and guide including an integrated displacement translator and targeting arm, in accordance with some embodiments.

FIG. 18 illustrates a targeting guide 400a including a fixed handle body 402a, in accordance with some embodiments. The targeting guide 400a is similar to the targeting guide 400 discussed above, and similar description is not repeated herein. The targeting guide 400a includes a fixed handle body 402a having a generally rounded rectangular shape and defining an inner cavity 404. The targeting guide 400a is fixedly coupled to a targeting arm 430a extending substantially along a longitudinal axis 434. The targeting arm 430a defines a cutting guide slot 460. The cutting guide slot 460 is sized and configured to receive a surgical tool, such as a burr 60 therein (see FIG. 20). The targeting arm includes a plurality of slots 438a-438e sized and configured to receive a targeting body 450 therein.

Figure 19:
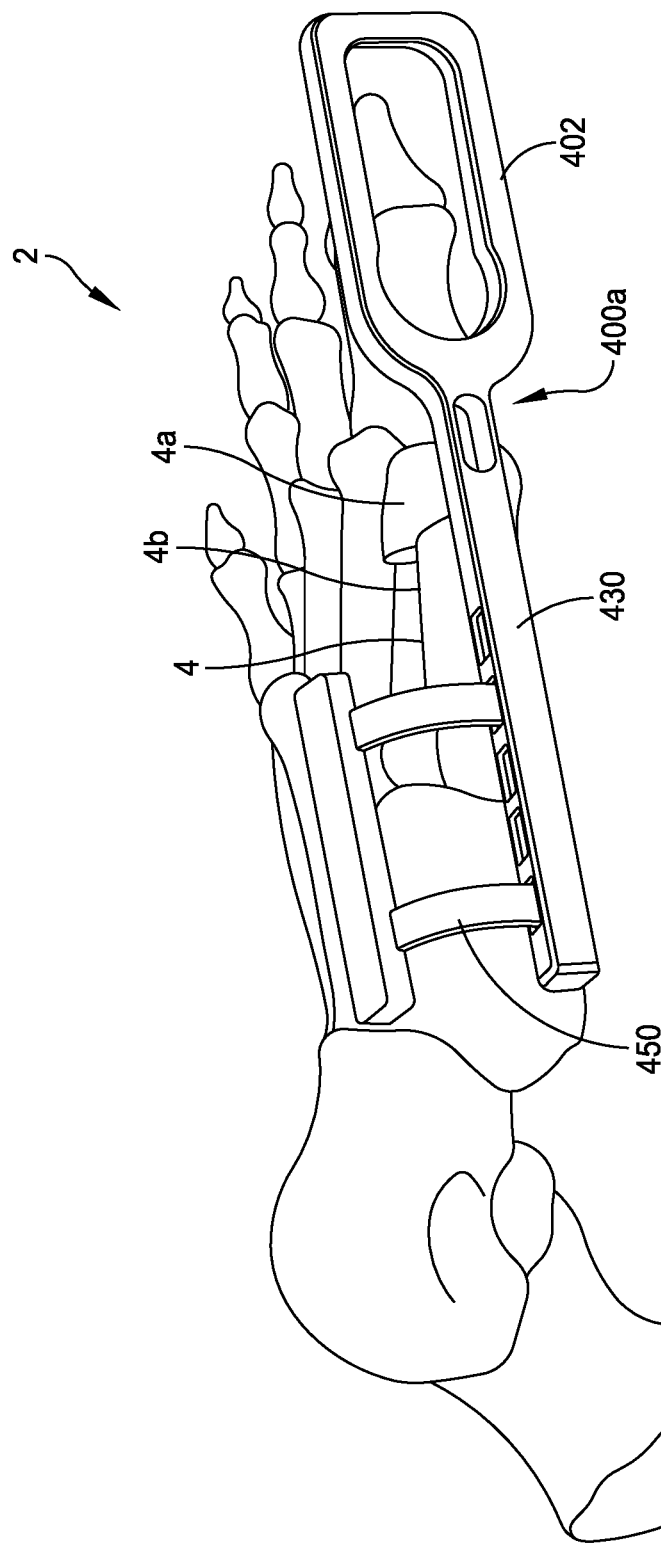
FIG. 19 illustrates the MIS combination displacement translator and guide of FIG. 18 positioned adjacent to a foot, in accordance with some embodiments.
Figure 20:
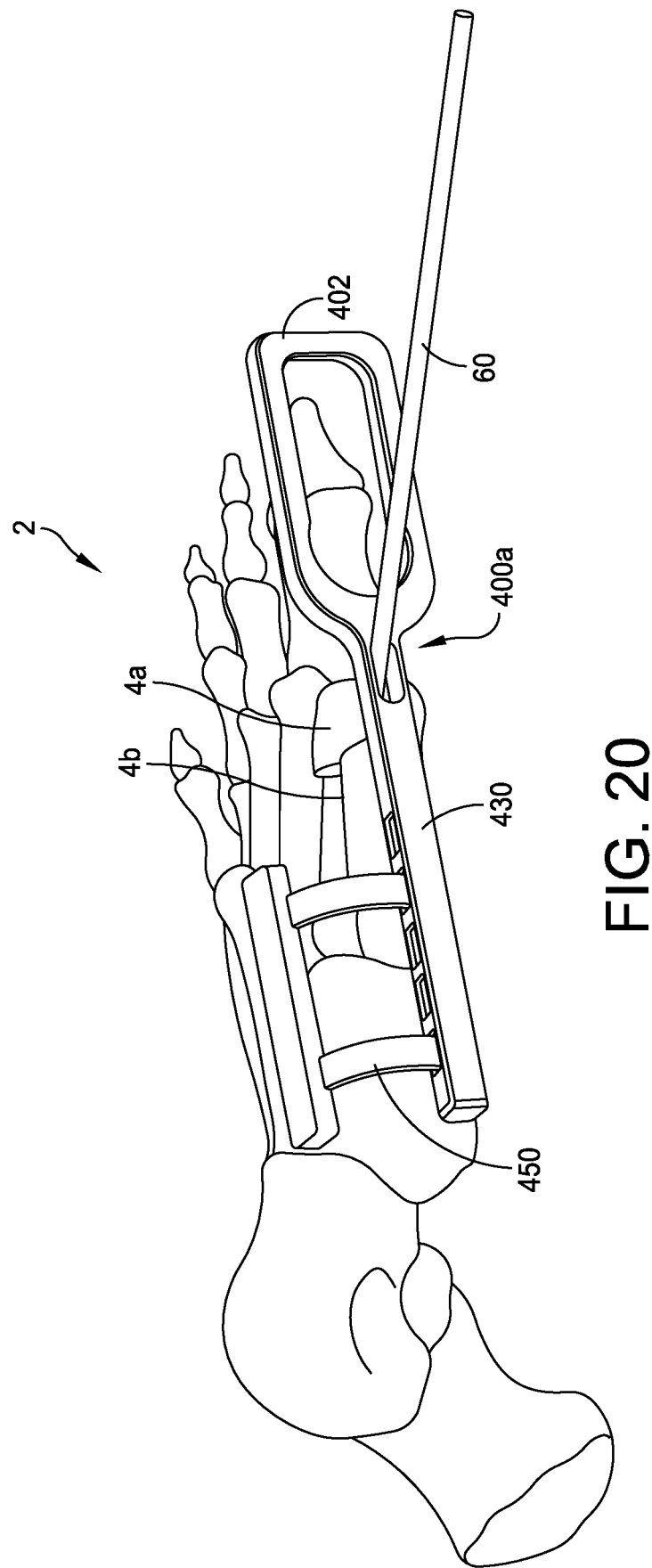
FIG. 20 illustrates a burr inserted through a cutting guide portion of the MIS combination displacement translator and guide of FIG. 19, in accordance with some embodiments.

In use, and as shown in FIG. 19, the targeting guide 400a is positioned adjacent to a first bone 4. The targeting 400a may be imaged, for example using fluoroscopy, to confirm alignment of the targeting guide 400a with the first bone 4. After confirming alignment, and as shown in FIG. 20, a burr 60 may be inserted through a cutting guide slot 460 to form an osteotomy in the first bone 4. After forming the osteotomy, the targeting guide 400a may be used to target and/or align one or more guide element for insertion into the first bone 4, as discussed in above.

Figure 21:
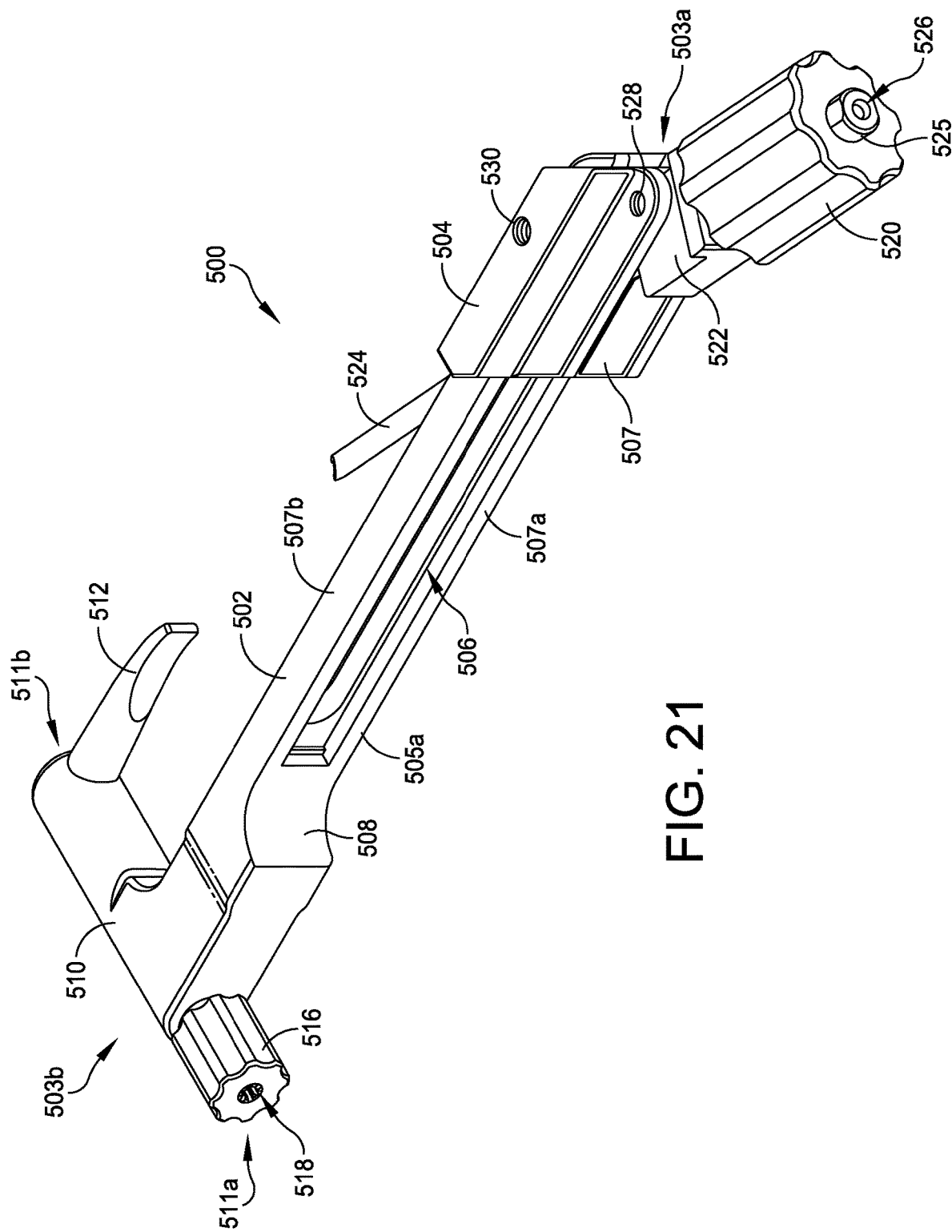
FIG. 21 illustrates a MIS integrated displacement translator and targeting arm, in accordance with some embodiments.
Figure 22:
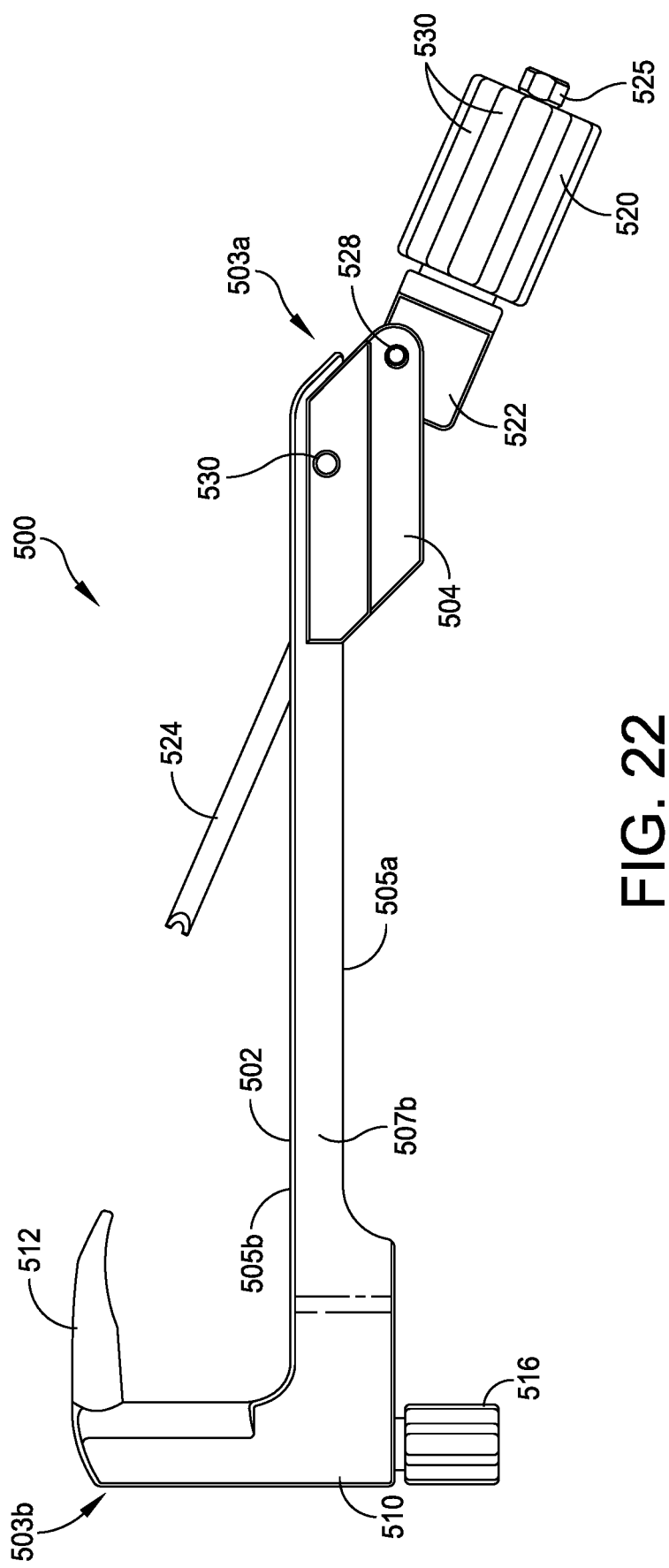
FIG. 22 illustrates a side view of the MIS integrated displacement translator and targeting arm of FIG. 21, in accordance with some embodiments.
Figure 23:
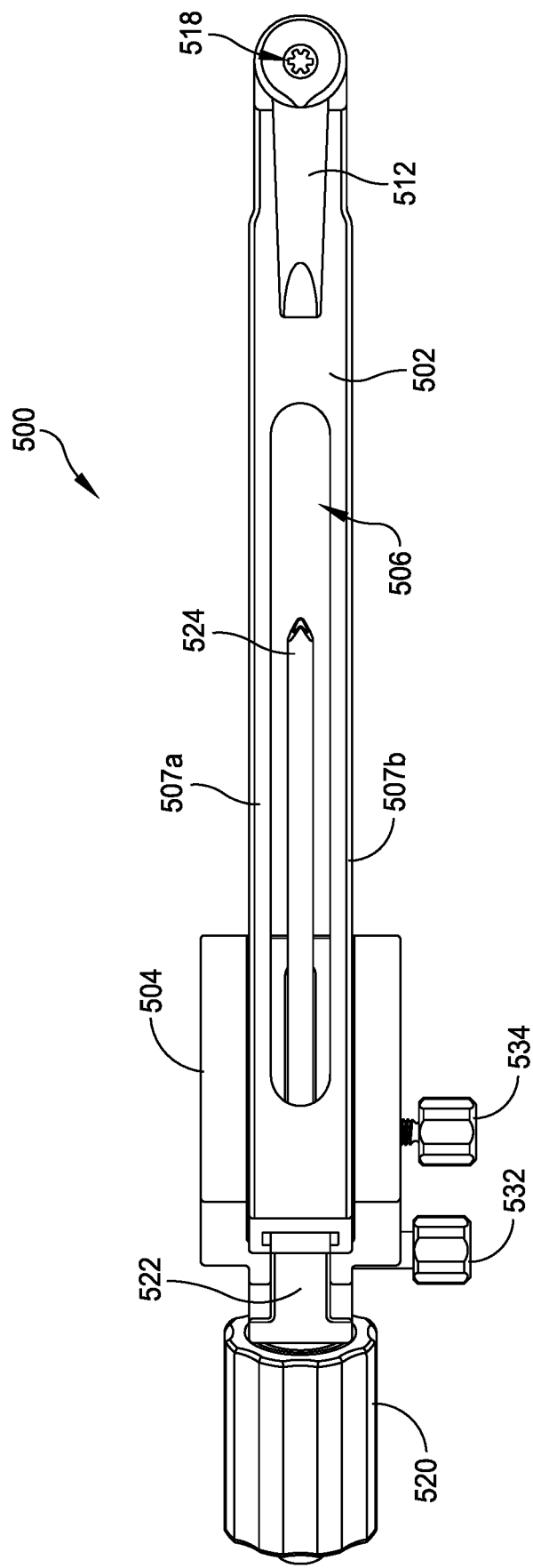
FIG. 23 illustrates a top-down view of the MIS integrated displacement translator and targeting arm of FIG. 21, in accordance with some embodiments.

FIGS. 21-23 illustrate a combination displacement and targeting surgical tool 500, in accordance with some embodiments. The combination displacement and targeting surgical tool 500 is similar to the displacement and surgical tools 100-400 described above, and similar description is not repeated herein. The combination displacement and targeting surgical tool 500 includes a handle body 502 extending from a first end 503a to a second end 503b. The handle body 502 includes a slot or longitudinal opening 506 defined by a first rail 507a and a second rail 507b spaced apart from the first rail 506a. The slot 506 extends through the body 502 from a first side 505a to a second side 505b.

In some embodiments, a head portion 510 is coupled to the body 502 by an offset or thickened portion 508. The head portion 510 includes a guide hole 518 defined at least partially by a guide head 516. The guide hole 518 extends from a first end 511a of the head portion 510 to a second end 511b of the head portion 510 substantially on a longitudinal axis that is substantially perpendicular to the longitudinal axis of the handle body 502. The guide hole 518 is sized and configured to receive a guide element, such as a k-wire, therethrough.

In some embodiments, a displacement tip 512 extends from the head portion 510. The displacement tip 512 may extend at any suitable angle with respect to the head portion 510. For example, in the illustrated embodiment, the displacement tip 512 extends substantially along a longitudinal axis that is substantially parallel to the longitudinal axis of the head portion 510. The displacement tip 512 is similar to the displacement tip 112 discussed above in conjunction with displacement translator 100, and similar description is not repeated herein. The displacement tip 512 may include a curved and/or straight profile. For example, in the illustrated embodiment, the displacement tip 512 defines a generally straight profile, although it will be appreciated that any suitable curved profile may also be used.

A slideable guide portion 504 is slideably coupled to the body 502 via the first and second rails 507a, 507b. For example, in some embodiments, the slideable guide portion 504 includes a slide body 507 defining at least one channel sized and configured to receive the first rail 507a and/or the second rail 507b of the handle body 502 therein. In some embodiments, the slideable guide portion 504 may include a slide element sized and configured to be received within the slot 506 defined by the handle body 502. Although specific embodiments are discussed herein, it will be appreciated that any suitable mechanism may be used to slideably couple the slideable guide portion 504 to the handle body 502.

In some embodiments, the slideable guide portion 504 includes a pivoting guide element 520 coupled to the slide body 507 in a pivoting arrangement. The pivoting guide element 520 includes a handle portion 521 and a pivoting body 522 each defining a guide hole 526 sized and configured to receive a guide element 524 therethrough. The pivoting guide element 520 may be pivoted with respect to the handle body 502 to change the angle defined between the guide element 524 and the handle body 502.

In some embodiments, the slideable guide portion 504 defines a first hole 528 sized and configured to receive a fixation element 532 (see FIG. 23) therein. The fixation element 532 is configured to lock or maintain the pivoting body 522 at a selected angle with respect to the handle body 502. In the illustrated embodiment, the first hole 528 includes an internal thread configured to couple to an external thread defined by the fixation element 532. The fixation element 532 may extend into a hole defined in the pivoting body 522 to lock the pivoting body 522 at the preselected angle. In other embodiments, the fixation element 532 may provide a friction or other locking mechanism with respect to the pivoting body 522.

In some embodiments, the slideable guide portion 504 defines a second hole 530 sized and configured to receive a fixation element 534 (see FIG. 23) therein. The fixation element 534 is configured to lock or maintain a longitudinal position of the slideable guide portion 504 with respect to the handle body 502. In the illustrated embodiment, the second hole 530 includes an internal thread configured to couple to an external thread defined by the fixation element 534. The fixation element 534 may provide friction or other locking mechanism with respect to the handle body 502 to maintain the slideable guide portion 504 at a selected longitudinal position with respect to the handle body 502.

Figure 24:
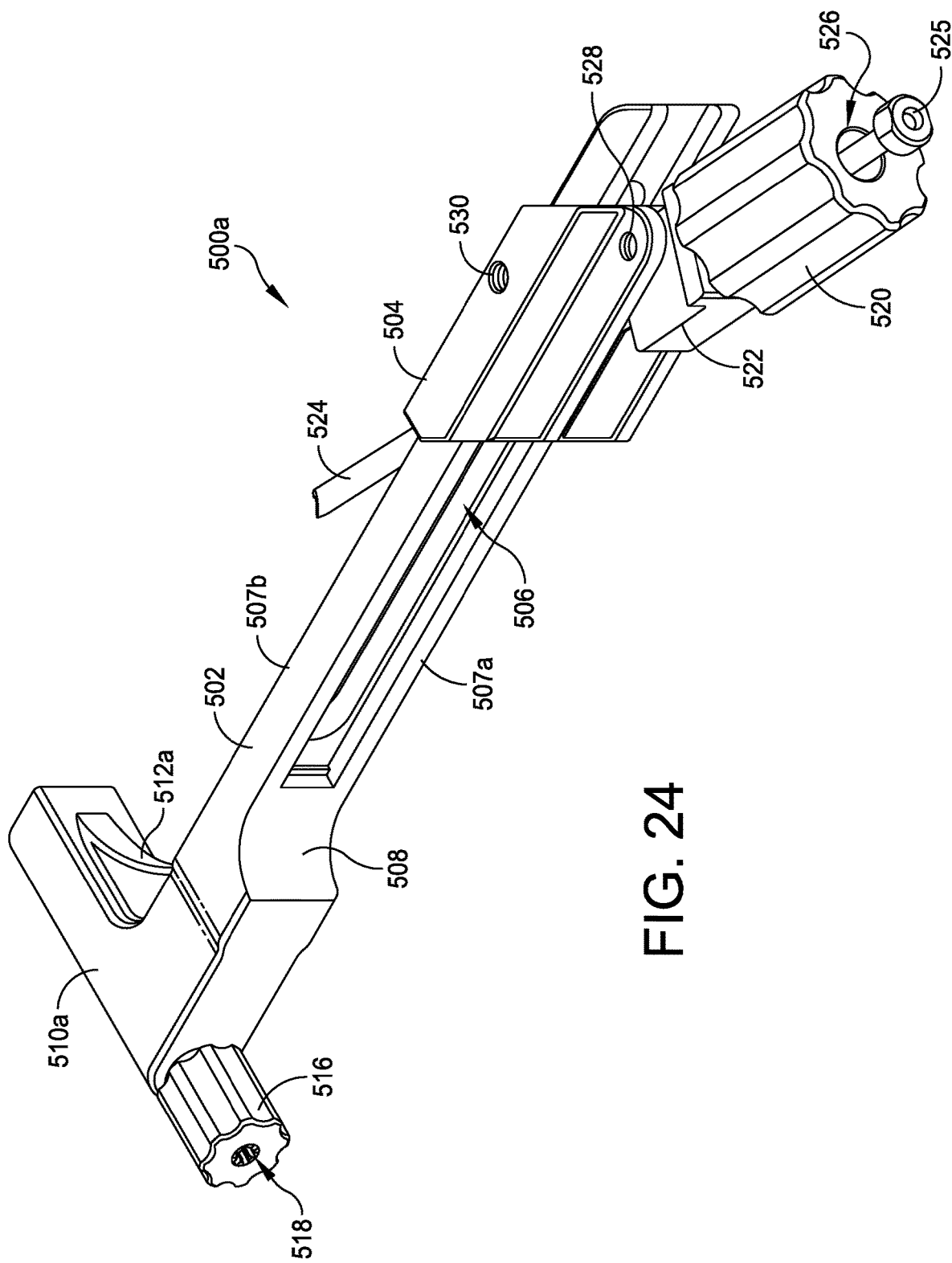
FIG. 24 illustrates a MIS integrated displacement translator and targeting arm, in accordance with some embodiments.
Figure 25:
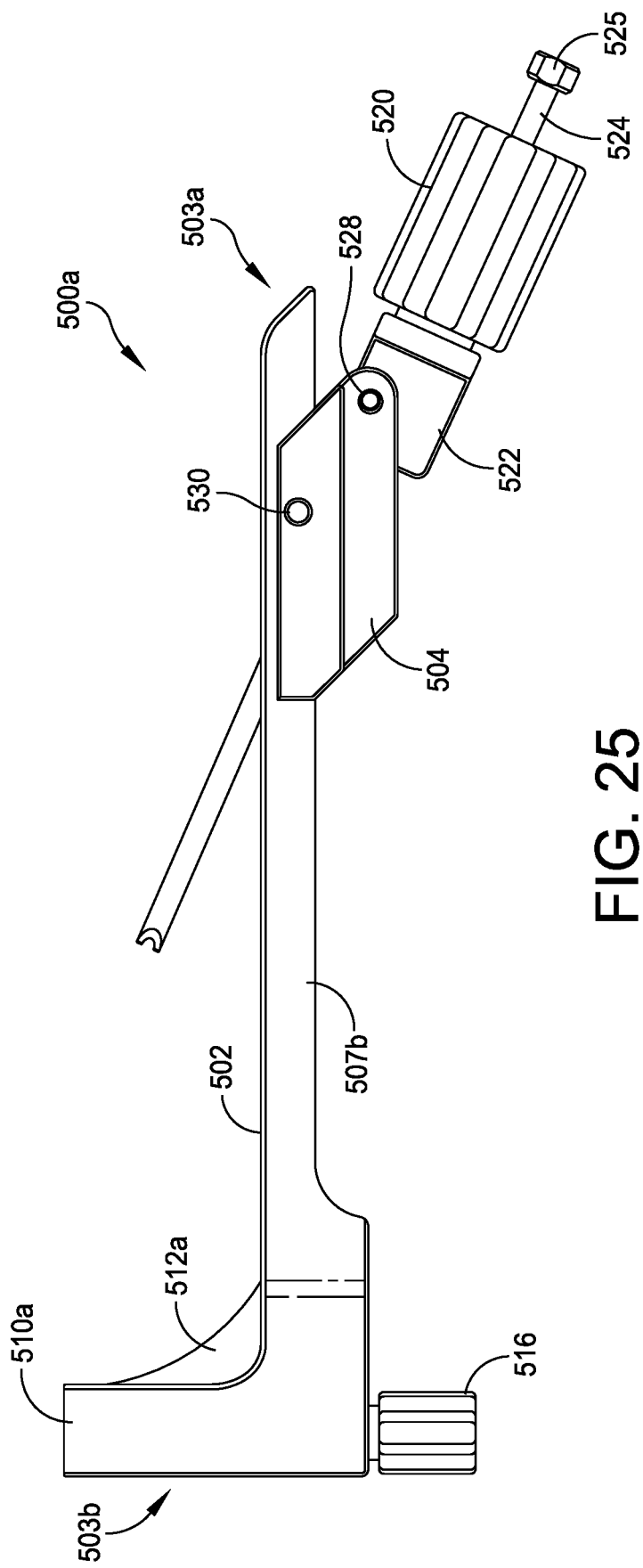
FIG. 25 illustrates a side view of the MIS integrated displacement translator and targeting arm of FIG. 24, in accordance with some embodiments.
Figure 26:
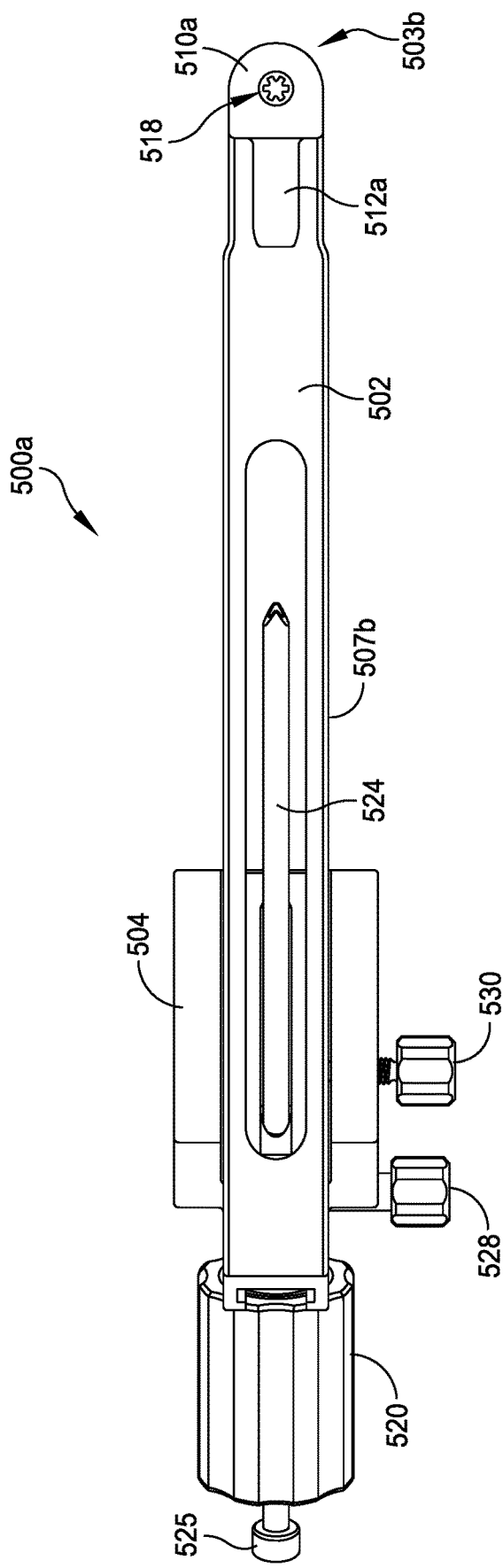
FIG. 26 illustrates a top-down view of the MIS integrated displacement translator and targeting arm of FIG. 24, in accordance with some embodiments.

FIGS. 24-26 illustrate a combination displacement and targeting surgical tool 500a, in accordance with some embodiments. The combination displacement and targeting surgical tool 500a is similar to the combination displacement and surgical tool 500 described above, and similar description is not repeated herein. The combination displacement and targeting surgical tool 500a includes a displacement tip 512a that extends substantially parallel to the longitudinal axis of the head 510a. The displacement tip 512a extends from the head portion 510a at a location that is substantially parallel with the handle body 502. The displacement tip 512a is similar to the displacement tip 112 discussed above in conjunction with displacement translator 100, and similar description is not repeated herein. The displacement tip 512a may include a curved and/or straight profile. For example, in the illustrated embodiment, the displacement tip 512a defines a generally curved profile, although it will be appreciated that any suitable profile may also be used.

Although the subject matter has been described in terms of exemplary embodiments, it is not limited thereto. Rather, the appended claims should be construed broadly, to include other variants and embodiments, which may be made by those skilled in the art.

What is claimed is:

1. A surgical tool, comprising:
   a handle body extending substantially on a first longitudinal axis;
   a displacement tip coupled to a first end of the handle body, the displacement tip extending substantially parallel to the first longitudinal axis; and
   an arm extension extending substantially on a second longitudinal axis, wherein a first end of the arm extension is coupled to the handle body; and
   a targeting arm pivotably coupled to a second end of the arm extension by a pivoting connection, the targeting arm defining at least one guide hole extending therethrough,
   wherein the targeting arm is configured to be lengthened or shortened to adjust a distance between the handle body and the targeting arm.

2. The surgical tool of claim 1, wherein the targeting arm comprises a pivoting targeting head including a targeting body defining the at least one guide hole.

3. The surgical tool of claim 2, wherein the pivoting targeting head is coupled to the targeting arm with a hinge.

4. The surgical tool of claim 1, wherein the displacement tip is slideably received within a channel defined in the handle body.

5. The surgical tool of claim 1, wherein the arm extension defines a channel sized and configured to receive a portion of the targeting arm therein.

6. The surgical tool of claim 5, wherein the channel comprises a closed channel.

7. The surgical tool of claim 1, wherein the targeting arm comprises:
   a first longitudinal portion extending substantially on a third longitudinal axis;
   a second longitudinal portion extending substantially on a fourth longitudinal axis; and
   a curved portion coupling the first longitudinal portion to the second longitudinal portion.

8. The surgical tool of claim 1, wherein the arm extension is adjustable to adjust a distance between the handle body and the targeting arm.

* * * * *